United States Patent [19]

Schmidt et al.

[11] 4,257,954

[45] Mar. 24, 1981

[54] NOVEL COMPOUNDS, PROCESSES AND MARKING SYSTEMS

[75] Inventors: Paul J. Schmidt, Sharonville; William M. Hung, Cincinnati, both of Ohio

[73] Assignee: Sterling Drug Inc., New York, N.Y.

[21] Appl. No.: 48,599

[22] Filed: Jun. 14, 1979

Related U.S. Application Data

[63] Continuation-in-part of Ser. No. 931,654, Aug. 8, 1978, abandoned.

[51] Int. Cl.³ .............................................. C07D 209/10
[52] U.S. Cl. .............................. 260/326.12 R; 546/94; 546/96; 546/273; 260/315; 260/326.35; 260/326.36; 260/326.47; 564/219; 564/315
[58] Field of Search ................................ 260/326.12 R

[56] References Cited

U.S. PATENT DOCUMENTS

| 3,193,404 | 7/1965 | Davis | 117/38 |
| 3,995,088 | 11/1976 | Garner et al. | 428/323 |

FOREIGN PATENT DOCUMENTS 2208611 9/1973 Fed. Rep. of Germany .
2243322 1/1975 Fed. Rep. of Germany .

OTHER PUBLICATIONS

Hellman, et al., "Chemische Berichte," vol. 98, 1965, p. 638.
Treibs, et al., "Chemical Abstracts", vol. 50, 1956, col. 944i.
Licari, et al., "Amer. Chem. Soc.", vol. 76, 1954, p. 4039.
Hinsberg, "Chemische Berichte," vol. 50, 1917, pp. 468–473.

*Primary Examiner*—Donald G. Daus
*Assistant Examiner*—James H. Turnipseed
*Attorney, Agent, or Firm*—Terrence E. Miesle; Lynn T. Fletcher; B. Woodrow Wyatt

[57] ABSTRACT

Mono and bis substituted (arylsulfonyl)alkanes useful as color formers, particularly in carbonless duplicating and thermal marking systems, are prepared by the interaction of the appropriate aldehyde or dialdehyde with the appropriate aryl or heterocyclic moiety and the appropriate phenylsulfinic acid in the presence of a catalyst.

15 Claims, No Drawings

NOVEL COMPOUNDS, PROCESSES AND MARKING SYSTEMS

CROSS REFERENCE TO RELATED APPLICATIONS

This application is a continuation-in-part of our co-pending application Ser. No. 931,654, filed Aug. 8, 1978, and now abandoned.

BACKGROUND OF THE INVENTION (a) Field of the Invention

This invention relates to novel compounds classified in the field of organic chemistry as [(aryl)(indolyl)(arylsulfonyl)]methanes; [(heteryl)(indolyl)(arylsulfonyl)]methanes; [(alkyl)(indolyl)(arylsulfonyl)]methanes; [bis(indolyl)-bis(arylsulfonyl)]alkanes; [bis(aryl)-(arylsulfonyl)]methanes; [(heteryl)(pyrrolyl)(arylsulfonyl)]methanes; [(aryl)(pyrrolyl)(arylsulfonyl)]methanes; and [(aryl)(heteryl)(arylsulfonyl)]methanes useful as color precursors, particularly in the art of carbonless dupblicating as, for example, in pressure-sensitive systems and in thermal marking systems; to processes for preparing said methanes and alkanes; and to pressure-sensitive duplicating systems and thermal marking systems.

(b) Description of the Prior Art

Several classes of organic compounds of widely diverse structural types are known to be useful as colorless precursors for carbonless duplicating systems. Among the more important classes, there may be named phenothiazines, for example, benzoyl leuco methylene blue; phthalides, for example, crystal violet lactone; fluorans, for example, 2'-anilino-6'-diethylaminofluoran and 2'-dibenzylamino-6'-diethylaminofluoran; arylsulfinate salts of Michler's Hydrol; and various other types of colorless precursors currently employed in commercially accepted carbonless copy systems. Typical of the many such systems taught in the prior art are those described in U.S. Pat. Nos. 2,712,507, 2,800,457, 3,041,289 and 4,000,087, which issued July 5, 1955, July 23, 1957, June 26, 1962 and Dec. 28, 1976, respectively. Many of the color formers in the prior art suffer one or more disadvantages such as low tinctorial strength, poor light stability, low resistance to sublimation, low susceptibility to copiability of the color-developed form in standard office copying machines, for example, a xerographic type of copier, and low solubility in common organic solvents, the latter disadvantage thus requiring the use of specialized and expensive solvents in order to obtain microencapsulated solutions of sufficient concentration for use in pressure-sensitive copying systems.

The following items to date appear to constitute the most relevant prior art with regard to the instant application.

Licari and Dougherty in the Journal of the American Chemical Society, 76, 4039 (1954) describe the preparation and physical properties of 3-indolemethyl phenyl sulfone and 3-indolemethyl p-toluenesulfone from gramine and the corresponding sulfinic acid or its salts. It is indicated that the compounds might have bacteriostatic or plant growth factor characteristics. Hellmann and Müller in Chemische Berichte, 98, 638 (1965) describe the preparation and physical characteristics of 3-benzolsulfonylmethylindol, 3-[p-toluolsulfonylmethyl]indol and 3-[p-chlorobenzolsulfonylmethyl]indol from the interaction of indole containing an active hydrogen, paraformaldehyde and a sulfinic acid sodium salt in a mixture of acetic acid and N,N-dimethylformamide. There is no indication of the utility of the compounds. We have now discovered that the class of compounds of the types described by Licari and Dougherty, and by Hellmann and Müller, are readily converted to colored substances on thermal exposure. This property makes them useful for incorporation into thermal marking systems such as are used in recording and in duplicating systems.

Treibs and Herrmann, in Hoppe-Seyler's Zeitschrift fuer Physiologische Chemie 299, 168–185 (1955) [Chemical Abstracts 50: 944i (1956)] describe the preparation and physical characteristics of (2-methyl-3-indolyl)(p-dimethylaminophenyl)methene perchlorate from the interaction of 2-methylindole and p-dimethylaminobenzaldehyde in perchloric acid. No indication of utility for the compounds is given in the abstract.

U.S. Pat. No. 3,995,088, issued Nov. 30, 1976, discloses in most pertinent part a series of normally colorless leuco methylene dyestuffs of the formula

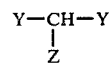

wherein Y represents an amino-substituted phenyl residue of the formula

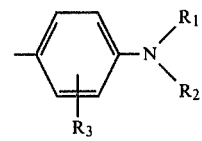

or an indolyl residue of the formula

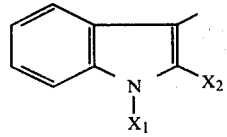

wherein $R_1$ and $R_2$, independently of the other represent hydrogen, alkyl with 1 to 12 carbon atoms, alkoxyalkyl with 2 to 8 carbon atoms, benzyl or phenyl, $R_3$ is hydrogen, halogen, nitro, alkyl having 1 to 4 carbon atoms or alkoxy having 1 to 4 carbon atoms, $X_1$ represents hydrogen, alkyl with 1 to 12 carbon atoms, alkenyl with at most 12 carbon atoms or benzyl, $X_2$ represents hydrogen, alkyl with 1 to 12 carbon atoms or phenyl and the ring A is unsubstituted or substituted by cyano, nitro, halogen, alkyl having 1 to 4 carbon atoms, alkoxy having 1 to 4 carbon atoms or acyl with 1 to 8 carbon atoms, and Z represents alkyl with 1 to 12 carbon atoms, alkenyl with at most 12 carbon atoms, aryl, aralkyl, an heterocyclic radical or the residue of an organic, particularly aliphatic or cycloaliphatic compound having a ketomethylene group. The compounds are claimed as being useful as color formers in pressure-sensitive copying paper.

U.S. Pat. No. 3,193,404, issued July 6, 1965, discloses in most pertinent part, a series of normally colorless associated dye salts derived from interaction of sulfinic acid and benzhydrols. The salts are stated to be useful as color formers in carbonless transfer sheets and are represented by the formula

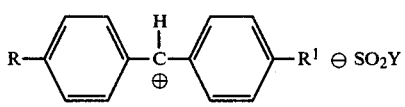

wherein R is dimethylamino, diethylamino or methoxy, $R^1$ is dimethylamino or diethylamino and Y is a $C_1$ to $C_{12}$ aliphatic group, phenyl or substituted phenyl.

German Offenlegungschrift No. 2,243,322, published Mar. 21, 1974, discloses in most pertinent part, a process for the preparation of a series of compounds having the formula

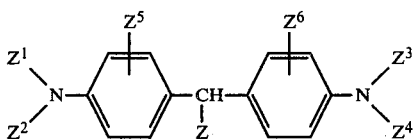

in which $Z^1$, $Z^2$, $Z^3$ and $Z^4$, independently of each other, signify hydrogen, if need be, substituted alkyl, cycloalkyl, aralkyl or aryl, and $Z^1$ and $Z^2$ and $Z^3$ and $Z^4$ together with the nitrogen represent a heterocycle or at times combined with one of the radicals at the ortho-position of the benzene ring produce a condensed heterocycle, and $Z^5$ is hydrogen, a halogen, an alkyl or alkoxy and $Z^6$ represents a hydrogen, halogen, alkyl or alkoxy and Z designates, if need be, a substituted aralkylamino, cycloalkylamino, arylamino, a radical bound via a heterocyclic nitrogen or arylsulfonyl. The compounds are said to be formed by the oxidation of a substituted diphenylmethane and subsequent reaction with a compound of the formula ZM wherein Z is as defined above and M is hydrogen, or a sodium, potassium or ammonium cation. The compounds are disclosed as being useful as reaction dyestuffs for carbonless copying procedures.

German Offenlegungschrift No. 2,208,611, which was published Sept. 6, 1973, discloses a process for the preparation of a series of compounds of the formula

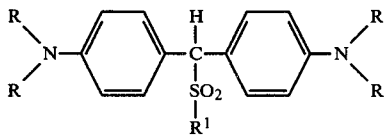

wherein R is methyl or ethyl and $R^1$ is phenyl or naphthyl substituted by an alkyl, chloro, nitro or alkoxy which comprises the condensation of the appropriate leucauramine of the formula

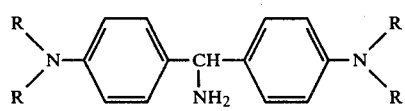

and a sulfinic acid of the formula $R^1$-$SO_2H$ in an acidic medium.

Hinsberg, in Chemische Berichte, 50 468–473 (1917), describes the preparation and physical properties of phenyl[4,4'-bis(dimethylamino)benzhydryl]sulfone prepared by the reaction of 4,4'-bis(dimethylamino)benzhydrol with benzene sulfonic acid in dilute hydrochloric acid. There is no indication of utility given for the product.

SUMMARY OF THE INVENTION

The present invention provides novel [(aryl)(indolyl)(arylsulfonyl)]methanes; [(heteryl)(indolyl)(arylsulfonyl)]methanes selected from among [bis(indolyl)-(arylsulfonyl)]methanes, [(pyrrolyl)(indolyl)(arylsulfonyl)]methanes, [(carbazolyl)(indolyl)(arylsulfonyl)]methanes, [(furanyl)(indolyl)(arylsulfonyl)]methanes, [(thienyl)(indolyl)(arylsulfonyl)]methanes, [(pyridinyl)(indolyl)(arylsulfonyl)]methanes, [(julolidinyl)(indolyl)(arylsulfonyl)]methanes; [(aryl)(indolyl)-(arylsulfonyl)]methanes; [bis(indolyl)-bis(arylsulfonyl)-]alkanes; [bis(aryl)(arylsulfonyl)]methanes; [(aryl)-(julolidinyl)(arylsulfonyl)]methanes; [(aryl)(pyrrolyl)-(arylsulfonyl)]methanes; [(thienyl)(pyrrolyl)(arylsulfonyl]methanes; [(furanyl)(pyrrolyl)(arylsulfonyl)]methanes; [bis(pyrrolyl)(arylsulfonyl)]methanes; [(pyridinyl)(pyrrolyl)(arylsulfonyl)]methanes; and [(carbazolyl)(pyrrolyl)(arylsulfonyl)]methanes which are useful as color precursors in pressure-sensitive duplicating systems and in thermal marking systems. The compounds develop colored images of good to excellent tinctorial strength and xerographic copiability and enhanced solubility in common organic solvents.

In one of its composition of matter aspects, the invention relates to a series of [(aryl)(indolyl)(arylsulfonyl)]methanes, [(heteryl)(indolyl)(arylsulfonyl)]methanes, [(alkyl)(indolyl)(arylsulfonyl)]methanes and [bis(indolyl)-bis(arylsulfonyl)]alkanes which are useful as color precursors in pressure-sensitive carbonless duplicating systems and thermal marking systems.

In the second of its composition of matter aspects, the invention relates to [bis(aryl)(arylsulfonyl)]methanes and [(aryl)(heteryl)(arylsulfonyl)]methanes which are useful as color precursors in pressure-sensitive carbonless duplicating systems and thermal marking systems.

In the third of its composition of matter aspects, the invention relates to [(heteryl)(pyrrolyl)(arylsulfonyl)]methanes and [(aryl)(pyrrolyl)(arylsulfonyl)]methanes which are useful as color precursors in pressure-sensitive carbonless duplicating systems and thermal marking systems.

In one of its process aspects, the invention relates to a process for preparing a [(A)(1-$R^1$-2-$R^2$-5/6-$R^3$-3-indolyl)(R-phenylsulfonyl)]methane which comprises interacting an aldehyde of the formula A-CHO with a 1-$R^1$-2-$R^2$-5/6-$R^3$-indole, and a R-phenylsulfinic acid in the presence of a catalyst.

In a second of its process aspects, the invention relates to a process for preparing a [αω-bis(indolyl)-α,ω-bis(arylsulfonyl)]alkane which comprises interacting a 1-$R^1$-2-$R^2$-5/6-$R^3$-indole and a R-phenylsulfinic acid with a dialdehyde, $(CH_2)_m(CHO)_2$, in the presence of a catalyst.

In a third of its process aspects, the invention relates to a process for preparing a [60 ,ω-bis(indolyl)-α,ω-bis-(arylsulfonyl)]butane which comprises interacting a 1-$R^1$-2-$R^2$-5/6-$R^3$-indole and a R-phenylsulfinic acid with a 2,5-di($C_1$-$C_3$ alkoxy)tetrahydrofuran, in the presence of a catalyst.

In a fourth of its process aspects, the invention relates to a process for preparing a [(Q)(2-$R^5$-4-$R^6$-phenyl)(R-phenylsulfonyl)]methane which comprises interacting an appropriate 2-$R^5$-4-$R^6$-benzaldehyde with a compound of the formula Q-H and an appropriate R-phenylsulfinic acid in the presence of a catalyst.

In a fifth of its process aspects, the invention relates to a process for preparing a [(Z)(1-R$^8$-2-pyrrolyl)(R-phenylsulfonyl)]methane which comprises interacting an appropriate aldehyde of the formula ZCHO with the appropriate 1-R$^8$ pyrrole and an appropriate R-phenylsulfinic acid in the presence of a catalyst.

The present invention provides as articles of manufacture pressure-sensitive carbonless duplicating systems and thermal marking systems each containing a color-forming substance comprising an [(aryl)(indolyl)(arylsulfonyl)]methane, a [(heteryl)(indolyl)(arylsulfonyl)]methane, an [(alkyl)(indolyl)(arylsulfonyl)]methane, a [bis(indolyl)-bis(arylsulfonyl)]alkane, a [bis(aryl)(arylsulfonyl)]methane or a [(aryl)(heteryl)(arylsulfonyl)]methane, [(heteryl)(pyrrolyl)(arylsulfonyl)]methane, or [(aryl)(pyrrolyl)(arylsulfonyl)]methane as well as mixtures thereof.

DETAILED DESCRIPTION INCLUSIVE OF THE PREFERRED EMBODIMENTS

More specifically, this invention, in its first composition of matter aspect, residues in the novel alkanes, which are particularly useful as colorless precursors in the art of carbonless duplicating and thermal marking, and which are [(A)(1-R$^1$-2-R$^2$-5/6-R$^3$-3-indolyl)(R-phenylsulfonyl)]methanes of the formula

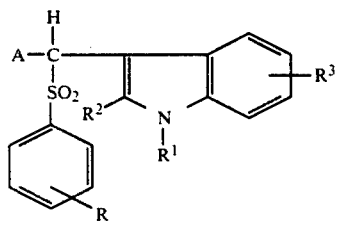

Formula I wherein: A represents a moiety selected from the class having the formulas

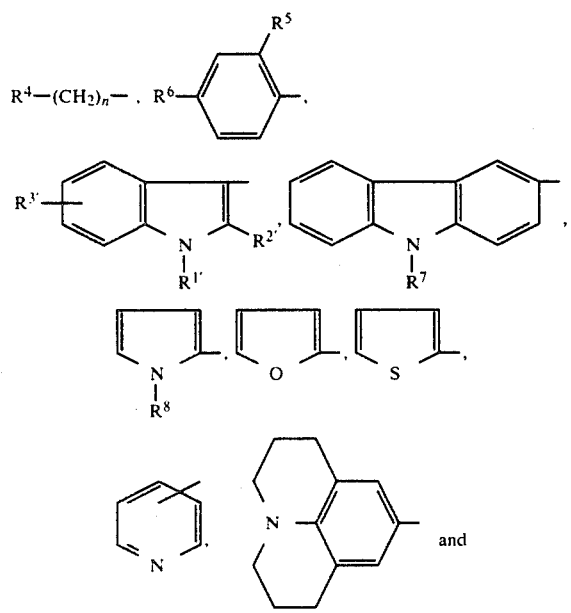

and

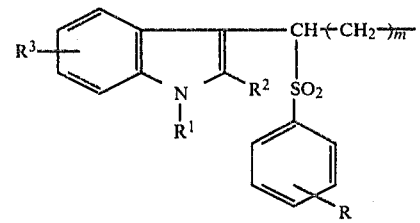

in which R represents one or two of hydrogen, $C_1$ to $C_{12}$ alkyl, $C_1$ to $C_3$ alkoxy, halo, nitro or acetamido; $R^1$ and $R^{1'}$ represent hydrogen, $C_1$ to $C_{18}$ alkyl, $C_2$ to $C_4$ alkenyl, benzyl or benzyl substituted in the benzene ring by one or two of halo or $C_1$ to $C_3$ alkyl; $R^2$ and $R^{2'}$ represent hydrogen, $C_1$ to $C_3$ alkyl or phenyl; $R^3$ and $R^{3'}$ represent one or two of hydrogen, $C_1$ to $C_3$ alkyl, $C_1$ to $C_3$ alkoxy, halo or nitro; $R^4$ represents hydrogen or methyl; $R^5$ represents hydrogen, dialkylamino in which alkyl is non-tertiary $C_1$ to $C_4$ alkyl, $C_1$ to $C_3$ alkyl, $C_1$ to $C_4$ alkoxy or halo; $R^6$ represents hydrogen, $C_1$ to $C_3$ alkyl, $C_1$ to $C_3$ alkoxy, halo, dialkylamino in which alkyl is non-tertiary $C_1$ to $C_4$ or N-alkylbenzylamino, in which alkyl is non-tertiary $C_1$ to $C_4$ and benzyl may be substituted in the benzene ring by one or two of halo or $C_1$ to $C_3$ alkyl; $R^7$ and $R^8$ represent hydrogen, $C_1$ to $C_3$ alkyl or phenyl; n is an integer from zero to ten with the proviso that when n is zero and $R^4$ is hydrogen or methyl, $R^1$, $R^2$ and $R^3$ cannot simultaneously be hydrogen; and m represents an integer from one to six.

In a first particular embodiment in accordance with the first composition of matter aspect, the invention sought to be patented resides in the novel [(2-R$^5$-4-R$^6$-phenyl)(1-R$^1$-2-R$^2$-5/6-R$^3$-3-indolyl)(R-phenylsulfonyl)]methanes of Formula I wherein A is 2-R$^5$-4-R$^6$-phenyl according to the formula

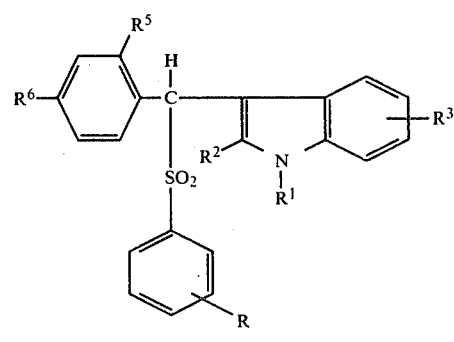

Formula II wherein R, $R^1$, $R^2$, $R^3$, $R^5$ and $R^6$ each have the same respective meanings given in Formula I.

In the second particular embodiment in accordance with the first composition of matter aspect, the invention sought to be patented resides in the novel [(1-R$^1$-2-R$^2$-5/6-R$^3$-3-indolyl)(1-R$^{1'}$-2-R$^{2'}$-5/6-R$^{3'}$-3-indolyl)(R-phenylsulfonyl)]methane of Formula I wherein A is 1-R$^{1'}$-2-R$^{2'}$-5/6-R$^{3'}$-3-indolyl according to the formula

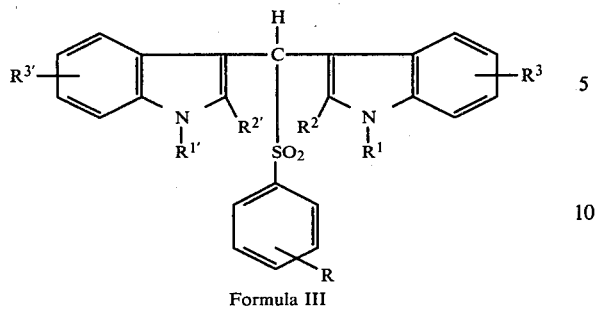

Formula III

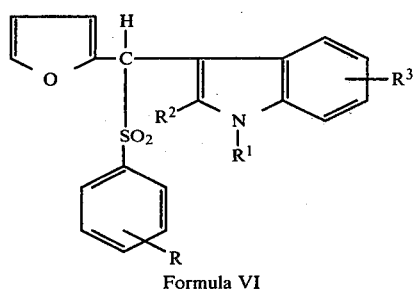

Formula VI wherein R, $R^1$, $R^{1'}$, $R^2$, $R^{2'}$, $R^3$ and $R^{3'}$ each have the same respective meanings given in Formula I.

In a third particular embodiment in accordance with the first composition of matter aspect, the invention sought to be patented resides in the novel [(9-$R^7$-3-carbazoyl)(1-$R^1$-2-$R^2$-5/6-$R^3$-3-indolyl)(R-phenylsulfonyl)]methanes of Formula I wherein A is 9-$R^7$-3-carbazolyl according to the formula wherein R, $R^1$, $R^2$ and $R^3$ each have the same respective meanings given in Formula I.

In a sixth particular embodiment in accordance with the first composition of matter aspect, the invention sought to be patented resides in the novel [(2-thienyl)(1-$R^1$-2-$R^2$-5/6-$R^3$-3-indolyl)(R-phenylsulfonyl)]methanes of Formula I wherein A is 2-thienyl according to the formula

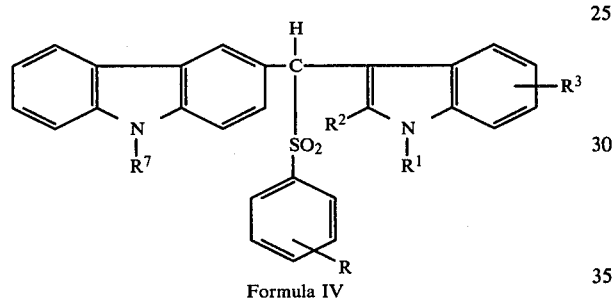

Formula IV

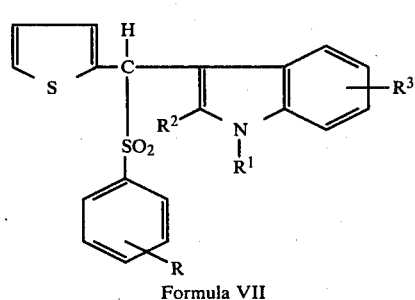

Formula VII wherein R, $R^1$, $R^2$, $R^3$ and $R^7$ each have the same meanings given in Formula I.

In a fourth particular embodiment in accordance with the first composition of matter aspect, the invention sought to be patented resides in the novel [1-$R^8$-2-pyrrolyl)(1-$R^1$-2-$R^2$-5/6-$R^3$-3-indolyl)(R-phenylsulfonyl)]methanes of Formula I wherein A is 1-$R^8$-2-pyrrolyl according to the formula wherein R, $R^1$, $R^2$ and $R^3$ each have the same respective meanings given in Formula I.

In a seventh particular embodiment in accordance with the first composition of matter aspect, the invention sought to be patented resides in the novel [(2-pyridinyl)(1-$R^1$-2-$R^2$-5/6-$R^3$-3-indolyl)(R-phenylsulfonyl)]methanes of Formula I wherein A is 2-pyridinyl according to the formula

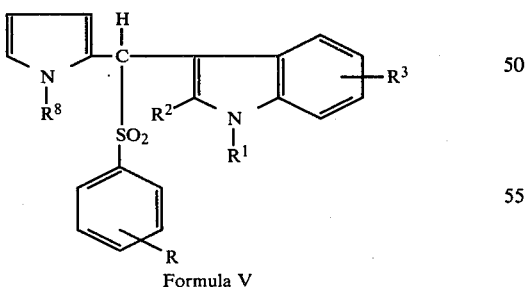

Formula V

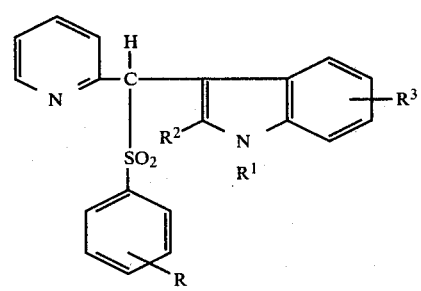

Formula VIII wherein R, $R^1$, $R^2$, $R^3$ and $R^8$ each have the respective meanings given in Formula I.

In a fifth particular embodiment in accordance with the first composition of matter aspect, the invention sought to be patented resides in the novel [(2-furanyl)(1-$R^1$-2-$R^2$-5/6-$R^3$-3-indolyl)(R-phenylsulfonyl)]methanes of Formula I wherein A is 2-furanyl according to the formula wherein R, $R^1$, $R^2$ and $R^3$ each have the same respective meanings given in Formula I.

In an eighth particular embodiment in accordance with the first composition of matter aspect, the invention sought to be patented resides in the novel [(9-julolidinyl)(1-$R^1$-2-$R^2$-5/6-$R^3$-3-indolyl)(R-phenylsulfonyl)]meythanes of Formula I wherein A is 9-julolidinyl according to the formula

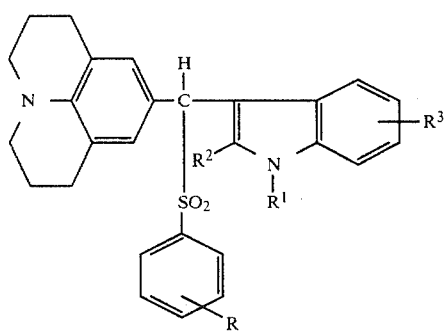

Formula IX wherein R, $R^1$, $R^2$ and $R^3$ each have the same respective meanings given in Formula I.

In a ninth particular embodiment in accordance with the first composition of matter aspect, the invention sought to be patented resides in the novel $\{[R^4\text{-}(CH_2)_m](1\text{-}R^1\text{-}2\text{-}R^2\text{-}5/6\text{-}R^3\text{-}3\text{-}indolyl)(R\text{-}phenyl\text{-}sulfonyl)\}$methanes of Formula I wherein A is $R^4\text{-}(CH_2)_n\text{-}$ according to the formula

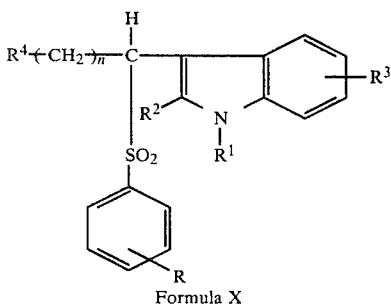

Formula X wherein R, $R^1$, $R^2$, $R^3$, $R^4$ and n each have the same respective meanings given in Formula I.

In a tenth particular embodiment in accordance with the first composition of matter aspect, the invention sought to be patented resides in the novel $[\alpha,\omega\text{-bis}(1\text{-}R^1\text{-}2\text{-}R^2\text{-}5/6\text{-}R^3\text{-}3\text{-}indolyl)\text{-}\alpha,\omega\text{-bis}(R\text{-}phenylsulfonyl)]$alkanes of Formula I wherein A is

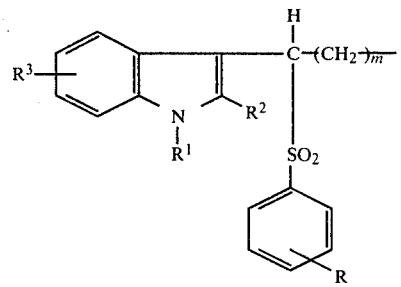

according to the formula

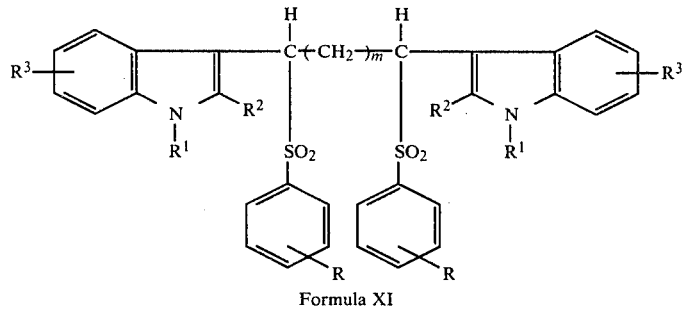

Formula XI wherein R, $R^1$, $R^2$ and $R^3$ each have the same respective meanings given in Formula I.

This invention, in its second composition of matter aspect, resides in the novel methanes, which are particularly useful as colorless precursors in the art of carbonless duplicating and thermal marking, and which are $[(B)(2\text{-}R^5\text{-}4\text{-}R^6\text{-}phenyl)(R\text{-}phenylsulfonyl)]$methanes having the formula

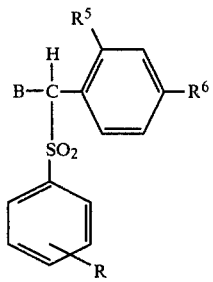

Formula XII wherein: B represents a moiety selected from the class having the formulas

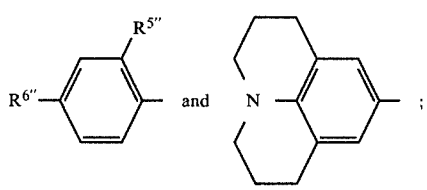

R represents one or two of hydrogen, $C_1$ to $C_{12}$ alkyl, $C_1$ to $C_3$ alkoxy, halo, nitro or acetamido; $R^5$ and $R^{5''}$ represent hydrogen, dialkylamino in which alkyl is non-tertiary $C_1$ to $C_4$ alkyl, $C_1$ to $C_3$ alkyl, $C_1$ to $C_4$ alkoxy or halo; $R^6$ represents hydrogen, $C_1$ to $C_3$ alkyl, $C_1$ to $C_3$ alkoxy, halo, dialkylamino in which alkyl is non-tertiary $C_1$ to $C_4$ or N-alkylbenzylamino in which alkyl is non-tertiary $C_1$ to $C_4$ and benzyl may be substituted in the benzene ring by one or two of halo or $C_1$ to $C_3$ alkyl; $R^{6''}$ represents hydrogen, $C_1$ to $C_3$ alkyl or halo with the provisos (i) that when $R^5$ or $R^{5''}$ is dialkylamino, $R^{6''}$ represents dialkylamino in which alkyl is non-tertiary $C_1$ to $C_4$ or N-alkylbenzyl amino in which alkyl is non-tertiary $C_1$ to $C_4$ and benzyl may be substituted in the benzene ring by one or two of halo or $C_1$ to $C_3$ alkyl and (ii) when $R^5$ or $R^{5''}$ is other than hydrogen, $R^{6''}$ is $C_1$ to $C_3$ alkoxy.

In a first particular embodiment in accordance with the second composition of matter aspect, the invention sought to be patented resides in the novel [(2-$R^{5''}$-4-$R^{6''}$-phenyl)(2-$R^5$-4-$R^6$-phenyl)(R-phenylsulfonyl)]methanes of Formula XII wherein B, is 2-$R^{5''}$-4-$R^{6''}$-phenyl according to the formula

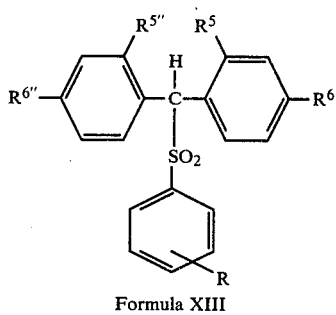

Formula XIII wherein R, $R^5$, $R^{5''}$, $R^6$ and $R^{6''}$ each have the same respective meanings given in Formula XII.

In a second particular embodiment in accordance with the second composition of matter aspect, the invention sought to be patented resides in the novel [(9-julolidinyl)(2-$R^5$-4-$R^6$-phenyl)(R-phenylsulfonyl)]methane of Formula XII wherein B is 9-julolidinyl according to the formula

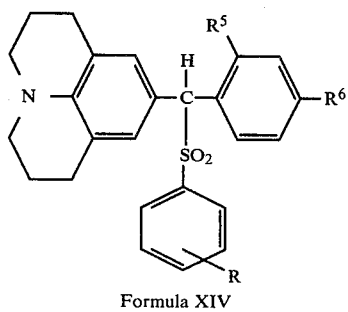

Formula XIV wherein R, $R^5$ and $R^6$ each have the same respective meanings given in Formula XII.

This invention, in its third composition of matter aspects, resides in the novel methanes, which are particularly useful as colorless precursors in the art of carbonless duplicating and thermal marking, and which are [(Z)(1-$R^8$-2-pyrrolyl)(R-phenylsulfonyl)]methanes having the formula

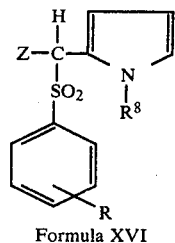

Formula XVI wherein Z represents a moiety selected from the class having the formulas

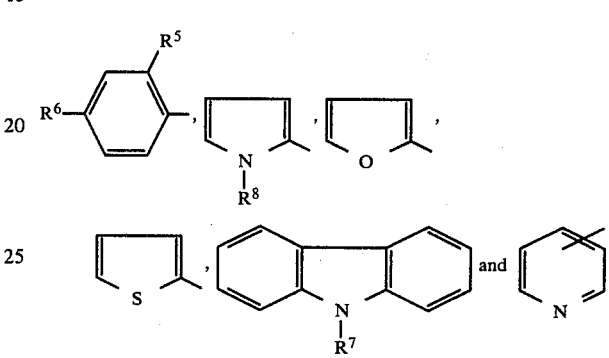

R represents one or two of hydrogen, $C_1$ to $C_{12}$ alkyl, $C_1$ to $C_3$ alkoxy, halo, nitro or acetamido; $R^5$ represents hydrogen, dialkylamino in which alkyl is non-tertiary $C_1$ to $C_4$ alkyl, $C_1$ to $C_3$ alkyl, $C_1$ to $C_4$ alkoxy or halo; $R^6$ represents hydrogen, $C_1$ to $C_3$ alkyl, $C_1$ to $C_3$ alkoxy, halo, dialkylamino in which alkyl is non-tertiary $C_1$ to $C_4$ or N-alkylbenzylamino in which alkyl is non-tertiary $C_1$ to $C_4$ and benzyl may be substituted in the benzene ring by one or two of halo or $C_1$ to $C_3$ alkyl; and $R^7$ and $R^8$ represent hydrogen, $C_1$ to $C_3$ alkyl or phenyl.

In a first particular embodiment in accordance with the third composition of matter aspect, the invention sought to be patented resides in the novel [(2-$R^5$-4-$R^6$-phenyl)(1-$R^8$-2-pyrrolyl)(R-phenylsulfonyl)]methanes of Formula XVI wherein Z is 2-$R^5$-4-$R^6$-phenyl according to the formula

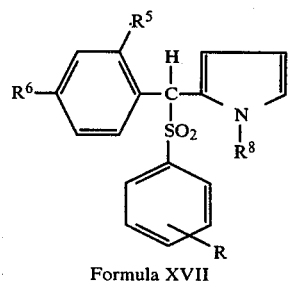

Formula XVII wherein R, $R^5$, $R^6$ and $R^8$ each have the same respective meanings given in Formula XVI.

In a second particular embodiment in accordance with the third composition of matter aspect, the invention sought to be patented resides in the novel [(2-thienyl)(1-$R^8$-2-pyrrolyl)(R-phenylsulfonyl)]methanes of Formula XVI wherein Z is 2-thienyl according to the formula

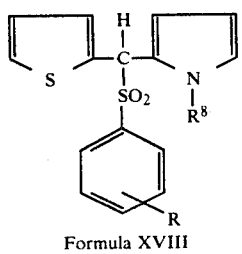

Formula XVIII wherein R and $R^8$ each have the same meanings given in Formula XVI.

In a third particular embodiment in accordance with the third composition of matter aspect, the invention sought to be patented resides in the novel [(2-furanyl)(1-$R^8$-2-pyrrolyl)(R-phenylsulfonyl)]methanes of Formula XVI wherein Z is 2-furanyl according to the formula

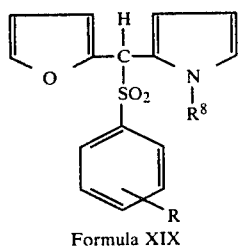

Formula XIX wherein R and $R^8$ each have the same meanings given in Formula XVI.

In a fourth particular embodiment in accordance with the third composition of matter aspect, the invention sought to be patented resides in the novel [(9-$R^7$-3-carbazolyl)(1-$R^8$-2-pyrrolyl)(R-phenylsulfonyl)]methanes of Formula XVI wherein Z is 9-$R^7$-3-carbazolyl according to the formula

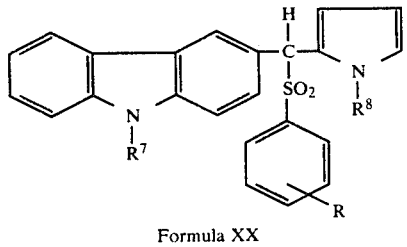

Formula XX wherein R, $R^7$ and $R^8$ each have the same meanings given in Formula XVI.

In one of its process aspects, the invention sought to be patented resides in a process for preparing a [(A)(1-$R^1$-2-$R^2$-5/6-$R^3$-3-indolyl)(R-phenylsulfonyl)]methane according to Formula I wherein A represents a moiety selected from the class having the formulas

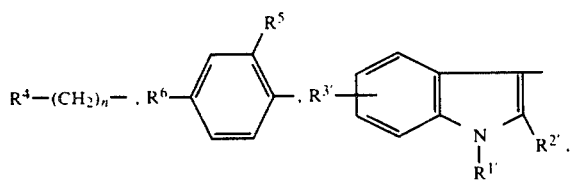

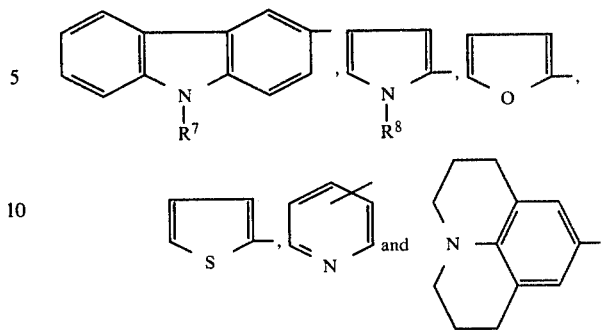

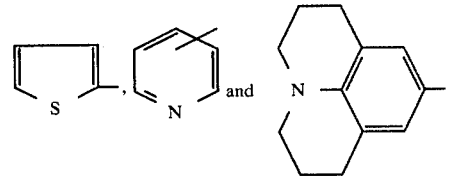

which comprises interacting in approximately equal molecular proportions an appropriate 1-$R^1$-2-$R^2$-5/6-$R^3$-indole with an R-phenylsulfinic acid and an appropriate aldehyde of the formula A-CHO in the presence of a catalyst wherein A is as above defined and each of R, $R^1$, $R^2$, $R^3$, $R^4$, $R^5$, $R^6$, $R^7$, $R^8$, $R^{1'}$, $R^{2'}$, $R^{3'}$ and n have the same respective meanings given in Formula I.

In a second of its process aspects, the invention sought to be patented resides in the process for preparing a [α,ω-bis(1-$R^1$-2-$R^2$-5/6-$R^3$-3-indolyl)-α,ω-bis(R-phenylsulfonyl)]alkane according to Formula XI which comprises interacting approximately two molecular proportions of an appropriate 1-$R^1$-2-$R^2$-5/6-$R^3$-indole with approximately two molecular equivalents of an appropriate R-phenylsulfinic acid and approximately one molecular equivalent of an appropriate dialdehyde of the formula $(CH_2)_m(CHO)_2$ in the presence of a catalyst wherein R, $R^1$, $R^2$, $R^3$ and m each have the same respective meanings given in Formula XI.

In a third of its process aspects, the invention sought to be patented resides in the process for preparing a [1,4-bis(1-$R^1$-2-$R^2$-5/6-$R^3$-3-indolyl)-1,4-bis(R-phenylsulfonyl)]butane according to Formula XI wherein m is two which comprises interacting approximately two molecular proportions of an appropriate 1-$R^1$-2-$R^2$-5/6-$R^3$-indole with approximately two molecular proportions of an appropriate R-phenylsulfinic acid and approximately one molecular proportion of an appropriate 2,5-di($C_1$-$C_3$alkoxy)tetrahydrofuran in the presence of a catalyst wherein R, $R^1$, $R^2$ and $R^3$ each have the same respective meanings given in Formula XI.

In a fourth of its process aspects, the invention sought to be patented resides in the process for preparing a [(Q)(2-$R^5$-4-$R^6$-phenyl)-(R-phenylsulfonyl)]methane having the formula

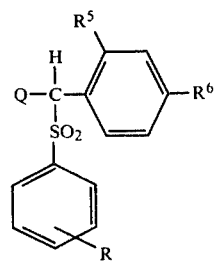

Formula XV wherein: Q represents a moiety selected from the class having the formulas

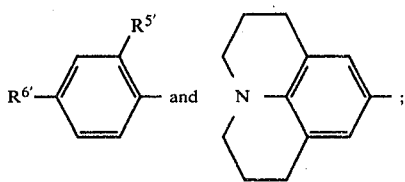

R represents one or two of hydrogen, $C_1$ to $C_{12}$ alkyl, $C_1$ to $C_3$ alkoxy, halo, nitro or acetamido; $R^5$ and $R^{5'}$ represent hydrogen, dialkylamino in which alkyl is non-tertiary $C_1$ to $C_4$ alkyl, $C_1$ to $C_3$ alkyl, $C_1$ to $C_4$ alkoxy or halo; and $R^6$ and $R^{6'}$ represent hydrogen, $C_1$ to $C_3$ alkyl, $C_1$ to $C_3$ alkoxy, halo, dialkylamino in which alkyl is non-tertiary $C_1$ to $C_4$ or N-alkylbenzylamino in which alkyl is non-tertiary $C_1$ to to $C_4$ and benzyl may be substituted in the benzene ring by one or two of halo or $C_1$ to $C_3$ alkyl; which comprises interacting in approximately equal molecular proportions an appropriate 2-$R^5$-4-$R^6$-benzaldehyde with an appropriate compound of the formula Q-H and an appropriate R-phenylsulfinic acid in the presence of a catalyst.

In a fifth of its process aspects, the invention sought to be patented resides in the process for preparing a [(Z)(1-$R^8$-2-pyrrolyl)(R-phenylsulfonyl)]methane according to Formula XVI wherein Z represents a moiety selected from the class having the formulas

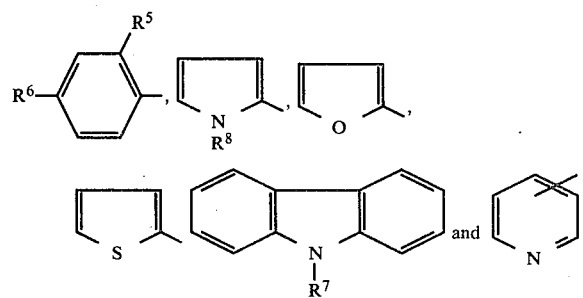

which comprises interacting in approximately equal molecular proportions an appropriate 1-$R^8$-pyrrole with a R-phenylsulfinic acid and an appropriate aldehyde of the formula Z-CHO in the presence of a catalyst wherein Z is as above defined and each of R and $R^8$ have the same respective meanings given in Formula XVI.

In its article of manufacture aspect, the invention sought to be patented resides in a pressure-sensitive carbonless duplicating system or a thermal marking system containing as a color-forming substance a [(A)(1-$R^1$-2-$R^2$-5/6-$R^3$-3-indolyl)(R-phenylsulfonyl)]methane according to Formula I, a [(B)(2-$R^5$-4-$R^6$-phenyl)(R-phenylsulfonyl)]methane according to Formula XII, a [α,ω-bis(1-$R^1$-2-$R^2$-5/6-$R^3$-indolyl)-α,ω-bis(R-phenylsulfonyl)]-alkane according to Formula XI or a [(Z)(1-$R^8$-2-pyrrolyl)(R-phenylsulfonyl)]methane according to Formula XVI wherein R, $R^1$, $R^2$, $R^3$, $R^5$, $R^6$, $R^8$, A, B and Z each have the same respective meanings given in relation to Formulas I, XI, XII or XVI.

A particular embodiment sought to be patented resides in a pressure-sensitive transfer sheet, adapted for use with a receiving sheet having an electron accepting layer, comprising a support sheet coated on one side with a layer of pressure-rupturable microcapsules containing a liquid solution of a color-forming substance comprising at least one compound depicted by Formula I, by Formula XII or by Formula XVI.

Another particular embodiment sought to be patented resides in a heat responsive record material comprising a support sheet coated on one side with a layer containing a mixture comprising at least one color-forming compound having Formula I, Formula XI, Formula XII or Formula XVI and an acidic developer arranged such that application of heat will produce a mark-forming reaction between the color-forming compound and the acidic developer.

Preferred articles within the ambit of the particular embodiments above described are those wherein the color-forming component comprises a [(2-$R^5$-4-$R^6$-phenyl)(1-$R^1$-2-$R^2$-5/6-$R^3$-indolyl)(R-phenylsulfonyl)]methane according to Formula II wherein R, $R^1$, $R^2$, $R^3$, $R^5$ and $R^6$ each have the same respective meanings given in relation to Formula II, a [(1-$R^1$-2-$R^2$-5/6-$R^3$-3-indolyl)(1-$R^{1'}$-2-$R^{2'}$-5/6-$R^{3'}$-3-indolyl)(R-phenylsulfonyl)]methane according to Formula III wherein R, $R^{1'}$, $R^2$, $R^{2'}$, $R^3$ and $R^{3'}$ each have the same respective meanings given in relation to Formula III, a [(2-furanyl)(1-$R^1$-2-$R^2$-5/6-$R^3$-3-indolyl)(R-phenylsulfonyl)]methane according to Formula VI wherein R, $R^1$, $R^2$ and $R^3$ each have the same respective meanings given in relation to Formula VI, a [(2-thienyl)(1-$R^1$-2-$R^2$-5/6-$R^3$-3-indolyl)(R-phenylsulfonyl)]methane according to Formula VII wherein R, $R^1$, $R^2$ and $R^3$ each have the same respective meanings given in relation to Formula VII, a [(1-$R^8$-2-pyrrolyl)(1-$R^1$-2-$R^2$-5/6-$R^3$-3-indolyl)(R-phenylsulfonyl)]methane according to Formula V wherein R, $R^1$, $R^2$, $R^3$ and $R^8$ each have the same respective meanings given in relation to Formula V, a [α,ω-bis(1-$R^1$-2-$R^2$-5/6-$R^3$-3-indolyl)-α,ω-bis(R-phenylsulfonyl)]alkane according to Formula XI wherein R, $R^1$, $R^2$ and $R^3$ each have the same respective meanings given in relation to Formula XI, a [(2-$R^{5''}$-4-$R^{6''}$-phenyl)(2-$R^5$-4-$R^6$-phenyl)(R-phenylsulfonyl)]methane according to Formula XIII wherein R, $R^5$, $R^{5'}$, $R^6$ and $R^{6'}$ each have the same respective meanings given in relation to Formula XIV, a [(2-$R^5$-4-$R^6$phenyl)(1-$R^8$-2-pyrrolyl)(R-phenylsulfonyl)]methane according to Formula XVII wherein R, $R^5$, $R^6$ and $R^8$ each have the same respective meanings given in relation to Formula XVII, a [(2-thienyl)(1-$R^8$-2-pyrrolyl)(R-phenylsulfonyl)]methane according to Formula XVIII wherein R and $R^8$ each have the same respective meanings given in relation to Formula XVIII or a [(9-$R^7$-3-carbazolyl)(1-$R^8$-2-pyrrolyl)(R-phenylsulfonyl)]methane according to Formula XX wherein R, $R^7$ and $R^8$ each have the same respective meanings given in relation to Formula XX.

The compounds of Formula I in which A is $R^4$—$(CH_2)_n$, the {[$R^4$—$(CH_2)_n$](1-$R^1$-2-$R^2$-5/6-$R^3$-3-indolyl)(R-phenylsulfonyl)}methanes depicted by Formula X, have also been found to produce colored images in red to purple shades when paper treated with them without an acid developer is contacted with a heated stylus or heated type. This group of compounds of the invention are decidedly advantageous over those compounds employed in thermal duplicating systems which require the incorporation of an acidic developer such as bisphenol A in that they afford thermal copy systems containing only a single component for the production of a colored image. Thus, in another of its aspects, this invention resides in a thermal paper marking system containing as a color forming substance a {[R$^4$-(CH$_2$)$_n$](1-R$^1$-2-R$^2$-5/6-R$^3$-3-indolyl)(R-phenylsulfonyl)}methane wherein R, R$^1$, R$^2$, R$^3$, R$^4$ and n each have the same respective meanings given in relation to Formula X.

As used herein the term "halo" includes chloro, fluoro, bromo and iodo. Chloro is the preferred halo substituent because of the relatively low cost and ease of preparation of the required chloro-substituted intermediates and because the other halogens offer no particular advantages over chloro. However, the other above-named halo substituents are also satisfactory.

The term dialkylamino in which alkyl is "non-tertiary $C_1$ to $C_4$ alkyl" denotes saturated, acyclic groups which may be straight or branched as exemplified by dimethylamino, diethylamino, ethylmethylamino, dipropylamino, dibutylamino, isobutylmethylamino and the like.

As used herein the terms "$C_1$ to $C_3$ alkyl", $C_1$ to $C_{12}$ alkyl" and "$C_1$ to $C_{18}$ alkyl" denote saturated monovalent straight or branched aliphatic hydrocarbon radicals including methyl, ethyl, propyl, isopropyl, butyl, isobutyl, tert-butyl, amyl, 1-methylbutyl, 3-methylbutyl, hexyl, isohexyl, heptyl, isoheptyl, octyl, isooctyl, 2-ethylhexyl, nonyl, 3-ethylheptyl, n-decyl, n-undecyl, n-dodecyl, n-tridecyl, n-tetradecyl, n-pentadecyl, n-hexadecyl, n-heptadecyl, n-octadecyl, 1,3,5-trimethylhexyl, 1,5-dimethyl-4-ethylhexyl, 5-methyl-2-butylhexyl, 2-propylnonyl, 2-butyloctyl, 2-pentylnonyl, 1,2-dimethylhexadecyl and the like.

The terms "$C_1$ to $C_3$" alkoxy and "$C_1$ to $C_4$ alkoxy" include saturated, acyclic, straight or branch-chained groups such as methoxy, ethoxy, propoxy, isopropoxy, butoxy, sec-butoxy, isobutoxy and tert-butoxy.

As used herein, the term "$C_2$ to $C_4$ alkenyl" means a monovalent aliphatic radical possessing a single double bond, for example, ethenyl (or vinyl), 2-propenyl (or allyl), 1-methylethenyl (or isopropenyl), 2-methyl-2-propenyl, 2-methyl-1-propenyl, 2-butenyl and 3-butenyl.

As used herein, the term "catalyst" denotes any material which will activate an aldehyde moiety and render it more susceptible to substitution. Among these catalysts are acidic halide Lewis acid catalysts, Bronsted acid catalysts, acidic oxide catalysts, acidic cation exchange resin catalysts, and any organic or inorganic material which is capable of partial hydrolysis in the reaction medium to form acidic conditions. Examples of catalysts are hydrobromic acid, hydrochloric acid, hydriodic acid, sulfuric acid, phosphoric acid, nitric acid, fluoroboric acid, perchloric acid, arylsulfonic acids and alkylsulfonic acids, for example, p-toluenesulfonic acid, methanesulfonic acid, formic acid, acetic acid, glycolic acid, lactic acid, propionic acid, monochloroacetic acid, dichloroacetic acid, trichloroacetic acid, trifluoroacetic acid, malonic acid, citric acid, fumaric acid, benzoic acid, salicylic acid, picric acid, trimellitic acid, aluminum chloride, ferric chloride, zinc chloride, stannic chloride, phosphorus trichloride, phosphorus pentachloride, boron trifluoride etherate, phosphorus oxychloride, thionyl chloride, ferric oxide, aluminum oxide, phosphorus pentaoxide, benzoyl chloride, benzoyl peroxide, potassium fluoride, sulfonated coals, sulfonated phenol-formaldehyde resins, sulfonated divinylbenzene cross linked polymers and exchangers with carboxyl group, phenol group or alumina-silicate skeleton. Further, the sulfinic acids which take part in the reaction may in some instances act as catalysts, thus alleviating the need to add a special catalyst to the reaction.

As used herein the term "reaction medium" denotes any non-solvent or solvent capable of dispersing, partially dissolving or completely dissolving the reactants thus providing a fluid medium for these reactants to interact forming the desired methanes. Examples of chemical compounds which may be utilized singly or in a combination as a "reaction medium" are methyl alcohol, ethyl alcohol, isopropyl alcohol, ethylene glycol, ethylene glycol monoethyl ether, propylene glycol, diethylene glycol, diethylene glycol dimethyl ether, toluene, chlorobenzene, 1-ethyl-2-methylindole, acetonitrile, ethylene dichloride, N,N-dimethylformamide, N,N-dimethylaniline, isopropyl crown ether and water.

The novel compounds of Formula I, those of Formula XV, which encompass the novel compounds of Formula XII and those of Formula XVI, hereinabove are essentially colorless in the depicted form. When contacted with an acidic medium for example, silica gel or one of the types ordinarily employed in pressure-sensitive carbonless duplicating systems such as silton clay or phenolic resins, the compounds of Formulas I, XV, and XVI develop a yellow through bluish-red to reddish-violet colored image of good to excellent tinctorial strength, and possessing excellent xerographic copiability and enhanced solubility in common organic solvents. The compounds are thus highly suitable for use as colorless precursors, that is, color-forming substances in pressure-sensitive carbonless duplicating systems. The darker violet colors can be used alone as color formers to produce images which are readily copiable, whereas the yellow, red and blue colors can be used as toners in admixture with other color formers to produce images of a neutral shade which desirably are readily copiable by xerographic means.

The compounds of this invention may be incorporated in any of the commercially accepted systems known in the carbonless duplicating art. A typical technique for such application is as follows. Solutions containing one or more colorless precursor compounds of Formulas I, XV and XVI optionally in admixture with other color formers, in suitable solvents are microencapsulated by well-known procedures for example as described in U.S. Pat. Nos. 3,649,649, 3,429,827 and 4,000,087. The microcapsules are coated on the reverse side of a sheet with the aid of a suitable binder and the coated transfer sheet is then assembled in a manifold with the microcapsule coated side in contact with a receiving sheet coated with an electron accepting substance, for example, silton clay or a phenollic resin. Application of pressure to the manifold such as that exerted by a stylus, typewriter or other form of writing or printing causes the capsules on the reverse side to rupture. The solution of the color former released from the ruptured microcapsules flows to the receiving sheet and on contact with the acidic medium thereon forms yellow to reddish-violet colored images of good tinctorial strength. It is, of course, obvious that variants of this mode of application can be utilized. For example, the receiving sheet in a manifold can alternatively be coated with the subject compounds and the acidic developing agent can be contained in microcapsules applied to the reverse side of the top sheet in the manifold; or the receiving sheet can be coated with a mixture containing both the acidic developing agent and the microencapsulated color former.

It has also been found that when the compounds of Formulas I, XV and XVI are intimately mixed with an acidic developer of the type generally employed in thermal papers such as described in U.S. Pat. No. 3,539,375, that is, papers which produce a colored image when contacted with a heated stylus or heated type, for example, bisphenol A, heating of the mixture produces a colored image of varying shades from yellow to reddish-violet depending on the particular compound of the invention employed. The ability of the compounds of Formulas I, XV and XVI to form a deep color when heated in admixture with an acidic developer such as bisphenol A, makes them useful in thermal paper marking systems, either where an original or a duplicate copy is prepared by contacting the thermal paper with a heated stylus or heated type in any of the methods generally known in the art.

The best mode contemplated by the inventors of carrying out this invention will now be described so as to enable any person skilled in the art to which it pertains to make and use the same.

In accordance with one of the process aspects of this invention, the [(A)(1-$R^1$-2-$R^2$-5/6-$R^3$-3-indolyl)(R-phenylsulfonyl)]methanes of Formula I are obtained by interacting approximately equal molecular proportions of an appropriate aldehyde of the formula A-CHO with an appropriate 1-2-$R^2$-5/6-$R^3$-indole and an appropriate R-phenylsulfinic acid wherein A, R, $R^1$, $R^2$ and $R^3$ have the same respective meanings given above in relation to Formula I. Similarly, in accordance with a second of the process aspects of this invention, the [(Q)(2-$R^5$-4-$R^6$-phenyl)(R-phenylsulfonyl)]methanes of Formula XV are obtained by interacting equal molecular proportions of the appropriate 2-$R^5$-4-$R^6$-benzaldehyde with an appropriate compound of the formula Q-H and an appropriate R-phenylsulfinic acid. The definition of Q, R, $R^5$ and $R^6$ are those given hereinabove in relation to Formula XV. In accordance with still another process aspect of this invention the [(Z)(1-$R^8$-2-pyrrolyl)(R-phenylsulfonyl)]methanes of Formula XVI are obtained by interacting approximately equal molecular proportions of an appropriate aldehyde of the formula Z-CHO with an appropriate 1-$R^8$-pyrrole and an appropriate R-phenylsulfinic acid wherein Z, R and $R^8$ have the same respective meanings given above in relation to Formula XVI. These reactions are conveniently carried out in a reaction medium as listed hereinabove, for example, a lower hydrocarbon chain alcohol or N,N-dimethylformamide in the presence of a catalyst selected from those listed hereinabove, at a temperature in the range of 5° to 150° C. for approximately one to thirty-five hours. The [(A)(1-$R^1$-2-$R^2$-5/6-$R^3$-3-indolyl)(R-phenylsulfonyl)]methane of Formula I, the [(Q)(2-$R^5$-4-$R^6$-phenyl)(R-phenylsulfonyl)]methane of Formula XV or the [(Z)(1-$R^8$-2-pyrrolyl)(R-phenylsulfonyl)]methanes of Formula XVI thus obtained can be isolated by filtration if the product is not soluble in the reaction medium or by the addition of a basic substance, for example, triethanolamine or ammonium hydroxide to effect precipitation of the methane. Alternatively, the reaction mixture can be poured into water or a dilute aqueous base, for example, ammonium hydroxide and the methane isolated by filtration or extracted with an organic solvent, for example, chlorobenzene or toluene followed by evaporation of the organic solvent leaving the product as a residue. The isolated methane can be purified by conventional means such as trituration, recrystallization or reslurrying with a suitable organic liquid.

In accordance with a further process aspect of the present invention, the [α,ω-bis(1-$R^1$-2-$R^2$-5/6-$R^3$-3-indolyl)-α,ω-bis(R-phenylsulfonyl)]alkanes of Formula XI can be prepared by interacting approximately two molecular proportions of a 1-$R^1$-2-$R^2$-5/6-$R^3$-indole and approximately two molecular proportions of a R-phenylsulfinic acid with approximately one molecular proportion of the appropriate aliphatic dialdehyde of the formula $(CH_2)_{\overline{m}}(CHO)_2$, wherein R, $R^1$, $R^2$ and $R^3$ each have the same respective meanings given in relation to Formula XV. The reaction is conveniently carried out in a manner similar to that described above for the preparation of the [(A)(1-$R^1$-2-$R^2$-5/6-$R^3$-3-indolyl)(R-phenylsulfonyl)]methanes of Formula I and the product is isolated in a similar manner.

In accordance with a third of the process aspects of this invention, the [1,4-bis(1-$R^1$-2-$R^2$-5/6-$R^3$-3-indolyl)-1,4-bis(R-phenylsulfonyl)]butanes of Formula XI can be prepared by interacting approximately two molecular proportions of a 1-$R^1$-2-$R^2$-5/6-$R^3$-indole and approximately two molecular proportions of a R-phenylsulfinic acid with approximately one molecular proportion of a 2,5-di($C_1$-$C_3$alkoxy)tetrahydrofuran. The reaction is conveniently carried out in a reaction medium selected from those listed hereinabove in the presence of a catalyst selected from those listed hereinabove, for example, hydrochloric acid in a temperature in the range of 5° to 50° C. for approximately one hour to eighteen hours. The [1,4-bis(1-$R^1$-2-$R^2$-5/6-$R^3$-3-indolyl)-1,4-bis(R-phenylsulfonyl)]butane thus obtained can be isolated by filtration.

The aliphatic, aromatic and heterocyclic aldehydes required as starting materials for the [(A)(1-$R^1$-2-$R^2$-5/6-$R^3$-3-indolyl)(R-phenylsulfonyl)]methanes of Formula I, the [α,ω-bis(R-phenylsulfonyl)]alkanes of Formula XI, the [(Q)(2-$R^5$-4-$R^6$-phenyl)(R-phenylsulfonyl)]methanes of Formula XV and the [(Z)(1-$R^8$-2-pyrrolyl)(R-phenylsulfonyl)methanes of Formula XVI constitute an old and well-known class of compounds many of which are commercially available or are readily obtained by conventional syntheses well known in the art. The following list of compounds exemplifies aliphatic, aromatic and heterocyclic aldehydes useful in carrying out the first step of the processes of this invention leading to the compounds of Formulas I, XI, XV and XVI.

Benzaldehyde,
2-Methylbenzaldehyde,
2-Chlorobenzaldehyde,
2-Methoxybenzaldehyde,
4-Methoxybenzaldehyde,
2-Bromobenzaldehyde,
4-Methylbenzaldehyde,
4-Chlorobenzaldehyde
2-Ethoxybenzaldehyde,
4-Ethoxybenzaldehyde,
2-Fluorobenzaldehyde,
4-Isopropylbenzaldehyde,
2,4-Dimethoxybenzaldehyde,
2-Chloro-4-dimethylaminobenzaldehyde,
3-Ethoxy-4-methoxybenzaldehyde,
2-Methoxy-4-dimethylaminobenzaldehyde,
2-Methoxy-4-diethylaminobenzaldehyde,
4-Dimethylaminobenzaldehyde,
4-Benzylaminobenzaldehyde,
5-methoxyindole-3-carboxaldehyde, 4-(N-Methylbenzylamino)benzaldehyde,
Indole-3-carboxaldehyde,
N-Methylpyrrole-2-carboxaldehyde,
2-Pyridinecarboxaldehyde,
3-Pyridinecarboxaldehyde,
4-Pyridinecarboxaldehyde,
Pyrrole-2-carboxaldehyde,
2-Thiophenecarboxaldehyde,
N-Ethyl-3-carbazolecarboxaldehyde,
2-Methyl-1-n-octylindole-3-carboxaldehyde,
1-n-Butyl-2-phenylindole-3-carboxaldehyde,
9-Formyljulolidine,
4-(N-Ethylbenzylamino)benzaldehyde,
1,2-Dimethylindole-3-carboxaldehyde,
1-Ethyl-2-phenylindole-3-carboxaldehyde,
4-Diethylaminobenzaldehyde,
2-Methyl-4-diethylaminobenzaldehyde,
1-Ethyl-2-methylindole-3-carboxaldehyde,
Formaldehyde,
Acetaldehyde,
Butylaldehyde,
Deconal,
Hexanal,
Heptaldehyde
Octyl aldehyde,
Propionaldehyde,
Valeraldehyde,
Glutaraldehyde, and
Nonyl aldehyde.

The indole compounds represented by 1-$R^1$-2-$R^2$-5/6-$R^3$-indole which are required to obtain the [(A)(1-$R^1$-2-$R^2$-5/6-$R^3$-3-indolyl)(R-phenylsulfonyl)]methanes of Formula I and the [$\alpha,\omega$-bis(1-$R^1$-2-$R^2$-5/6-$R^3$-3-indolyl)-$\alpha,\omega$-bis(R-phenylsulfonyl)]alkanes of Formula XI and the pyrrole compounds represented by 1-$R^8$-pyrrole which are required to obtain the [(Z)(1-$R^2$-2-pyrrole)(R-phenylsulfonyl)]methanes of Formula XVI form an old and well-known class of compounds readily obtained by conventional processes well known in the art. The following list of compounds exemplifies indole, pyrrole and carbazole compounds falling within the ambit of the formula 1-$R^1$-2-$R^2$-5/6-$R^3$-indole, pyrrole compounds falling within the ambit of the formula 1-$R^8$-pyrrole and carbazole compounds falling within the ambit of the formula 9-$R^8$-carbazole which are useful in the practice of the processes of this invention for producing the aforesaid methanes and alkanes of Formulas I, XI and XVI.

Indole
1-Methylindole,
2-Methylindole,
1,2-Dimethylindole,
1-Ethyl-2-methylindole,
2-Phenylindole,
1-Propyl-2-methylindole,
1-Benzyl-2-methylindole,
1-Butyl-2-methylindole,
1-Octyl-2-methylindole,
2-Ethyl-5-methylindole,
1-Benzyl-5-fluoroindole,
1-Methyl-6-nitroindole,
5-Methoxy-1-butylindole,
1-Allyl-2-methylindole,
1,2-Dimethyl-6-nitroindole,
1-(4-Chlorobenzyl)-2-methyl-5-nitroindole,
2-Ethylindole,
2-Ethyl-1-methylindole,
1-Isopropylindole,
2-Isopropylindole,
1-Methyl-5-bromo-6-nitroindole,
2,5,6-Trimethylindole,
1-Isobutyl-2-methylindole,
6-Bromo-2-methylindole,
1-Hexylindole,
1-(2,5-Dimethylbenzyl)-2-methylindole,
2-Propylindole,
6-Chloro-2-phenylindole,
1-(2-Ethylhexyl)-2-methylindole,
1-(2,6-Dichlorobenzyl)-2-methylindole,
1-Vinyl-2-methylindole,
2-Ethyl-6-methylindole,
6-Fluoro-1-benzylindole,
1(4-Bromobenzyl)-2-isopropylindole,
1-(3-Chlorobenzyl)-2-ethylindole,
5-Chloro-1-benzylindole,
1-(2-Fluorobenzyl)-2-methylindole,
5-Iodo-1-(1-methylhexyl)indole,
5,6-Dimethoxyindole,
1-(2-Methylbenzyl)-2-methylindole,
5,6-Dichloro-2-phenylindole,
1-Isoamylindole,
1-[3-(2-Methyl)-1-propenyl]-2-methoxyindole,
Pyrrole,
N-Methylpyrrole,
N-Ethylpyrrole,
N-Propylpyrrole,
N-Isopropylpyrrole,
N-Phenylpyrrole,
Carbazole,
9-Methylcarbazole,
9-Ethylcarbazole,
9-Propylcarbazole,
9-Isopropylcarbazole, and
9-Phenylcarbazole.

Benzenesulfinic acid and substituted benzenesulfinic acids required as intermediates for the methanes of Formulas I, XV and XVI and the alkanes of Formula XI form an old and well-known class of compounds. Further, it is well known in the art that sulfinic acids are unstable and can not be stored for periods of time. Generally speaking, the process aspects of this invention the sulfinic acid is generated in situ in the reaction medium by acidifying an alkali metal, alkaline earth metal, or ammonium salt of the sulfinic acid with a catalyst. The alkali metal, alkaline earth metal, or ammonium salts are readily obtainable by conventional procedures well known in the art. For example, benzenesulfonyl chloride is interacted with sodium sulfite and sodium bicarbonate in water to obtain the desired sodium benzenesulfinate, which per se is stable and can be stored until needed for reactions. The benzenesulfonyl chlorides are readily available from the interaction of phosphorus oxychloride on a benzenesulfonic acid or a salt thereof. The following compounds are exemplary of benzenesulfonyl chlorides useful in the preparation of these intermediates.

Benzenesulfonyl chloride,
p-Toluenesulfonyl chloride,
p-Bromobenzenesulfonyl chloride,
p-Chlorobenzenesulfonyl chloride,
4-Chloro-3-nitrobenzenesulfonyl chloride,
2,5-Dichlorobenzenesulfonyl chloride,
3,4-Dichlorobenzenesulfonyl chloride,
2,4-Dimethylbenzenesulfonyl chloride,
2,5-Dimethylbenzenesulfonyl chloride,
2,4-Dinitrobenzenesulfonyl chloride, p-Fluorobenzenesulfonyl chloride,
p-Iodobenzenesulfonyl chloride,
o-Nitrobenzenesulfonyl chloride,
m-Nitrobenzenesulfonyl chloride,
p-Nitrobenzenesulfonyl chloride,
4-Methoxybenzenesulfonyl chloride,
p-Acetamidobenzenesulfonyl chloride and
p-Dodecylbenzenesulfonyl chloride.

The aromatic and heterocyclic compounds represented by the formula Q-H, which are required for interaction with the 2-$R^5$-4-$R^6$-benzaldehydes and the R-phenylsulfinic acids to obtain the [(Q)(2-$R^5$-4-$R^6$-phenyl)(R-phenylsulfonyl)]methanes of Formula XV form old and well known classes of compounds readily obtained by conventional procedures well known in the art. The following list of compounds exemplifies aromatic and heterocyclic compounds falling within the ambit of the formula Q-H which are useful in the practice of the process of this invention for producing the aforesaid methanes of Formula XV.

N-Benzyl-N-sec-butylaniline,
N,N-Di-sec-butylaniline,
N,N-Diethyl-3-isopropylaniline,
N,N-Diisobutylaniline,
N,N-Diethyl-3-propoxyaniline,
N,N-Dipropylaniline,
N-Isopropyl-N-methylaniline,
N-Methyl-N-propylaniline,
N,N,N',N'-Tetrabutyl-m-phenylenediamine,
N,N-Dipropyl-o-anisidine,
N-Isobutyl-N-ethylaniline,
N,N,N',N'-Tetraethyl-m-phenylenediamine,
N-Propyl-N-ethylaniline,
N,N-Diethyl-3-ethylaniline,
N-Benzyl-N-sec-butyl-3-propoxyaniline,
N,N-Dimethyl-m-toluidine,
Julolidine
N,N,N',N'-Tetramethyl-m-phenylenediamine,
N,N-Dibutylaniline,
N,N-Diethyl-3-ethoxyaniline,
N,N-Diethyl-m-anisidine,
N,N-Dimethylaniline,
N-Benzyl-N-ethylaniline,
N,N-Diethyl-m-toluidine
N,N-Diethylaniline,
N-Ethyl-N-methylaniline,
N-Benzyl-N-methylaniline,
N-Benzyl-N-propylaniline,
N,N-Dimethyl-3-bromoaniline,
N,N,N',N'-Tetraisopropyl-m-phenylenediamine,
N,N-Dibutyl-3-fluoroaniline,
N-Benzyl-N-methyl-3-ethylaniline,
N,N,N',N'-Tetra-sec-butyl-m-phenylenediamine,
N-Benzyl-N-butyl-3-iodoaniline, and
N,N-Diisopropyl-3-chloraniline.

It will, of course, be understood by those skilled in the art of chemistry that the compounds of this invention may exist and may be represented in at least two tautomeric forms, namely, either as sulfones or as sulfinic acid esters. However, infrared and nuclear magnetic resonance spectroscopic determinations have established that the structure depicted by the formulas herein, namely, sulfones or sulfonyl derivatives is the most likely form to exist from the conditions of the reactions described herein.

The molecular structures of the compounds of this invention were assigned on the basis of the modes of synthesis and study of their infrared and nuclear magnetic resonance spectra.

The following examples will further illustrate the invention without, however, limiting it thereto. All melting points are uncorrected.

EXAMPLE 1

To a stirred mixture of 175.0 ml of ethyl alcohol, 27.5 ml of concentrated hydrochloric acid, 30.4 g (0.15 mole) of 86.4 percent sodium p-toluenesulfinate and 18.5 g (0.125 mole) of p-dimethylaminobenzaldehyde chilled to approximately 5° C., there was slowly added 19.5 g (0.113 mole) of 91.2 percent 1-ethyl-2-methylindole. The resulting mixture was stirred for approximately three and one half hours at ambient temperature, during which period the color changed from blue to yellow. The pH of the mixture was adjusted to approximately 8 by the addition of 40.0 g of triethanolamine and, after stirring approximately twenty minutes at room temperature, the temperature was raised to and maintained at 55°-60° C. for approximately twenty minutes. After cooling to approximately 10° C., the separated pink solid was collected by filtration and washed with 100.0 ml of cold ethyl alcohol. The solid was then suspended in a mixture of 350.0 ml of water and 10.0 g of triethanolamine at ambient temperature for approximately thirty minutes, collected by filtration and washed first with 150.0 ml of 3 percent aqueous triethanolamine and finally with 150.0 ml of water. After drying in vacuo at 40° C., there was obtained 42.2 g of [(4-dimethylaminophenyl)(1-ethyl-2-methyl-3-indolyl)(4-methylphenylsulfonyl)]methane (Formula II: R=4—$CH_3$; $R^1$=$C_2H_5$; $R^2$=$CH_3$; $R^3$=$R^5$=H; $R^6$=N($CH_3$)$_2$) which softened at 155° C. and melted at 159°-161° C.

Significant infrared maxima appeared at 1310 ($SO_2$; m) and 1145 ($SO_2$; m) cm$^{-1}$. The nuclear magnetic resonance spectral analysis was concordant with the assigned structure.

A toluene solution of this product contacted with an acidic clay, silica gel or a phenolic resin developed a bluish-red colored image.

EXAMPLE 2

With stirring, 3.8 g (0.025 mole) of p-dimethylaminobenzaldehyde was added to a mixture of 5.0 ml of concentrated hydrochloric acid, 35.0 ml of ethyl alcohol, 9.6 g (0.03 mole) of 55.6 percent sodium p-toluenesulfinate and 2.9 g (0.025 mole) of 1,2-dimethylindole. After stirring approximately one hour with heating at 55°-60° C., the resultant mixture was cooled to approximately 40° C. and 25.0 ml of ethyl alcohol was added. Then, 300 ml of water and 200 g of ice were slowly added to the mixture with stirring and the resulting solid was collected by filtration and washed with water. The water-wet filter cake was resuspended in 60.0 ml of chilled isopropyl alcohol and sufficient ammonium hydroxide to maintain slightly alkaline conditions. After stirring for approximately forty-five minutes at 5°-10° C., the suspended solid was recollected by filtration, washed with 15.0 ml of fresh isopropyl alcohol and dried at 45° C. in vacuo to obtain 8.9 g of [(4-dimethylaminophenyl)(1,2-dimethyl-3-indolyl)(4-methylphenylsulfonyl)]methane (Formula II: R=4—$CH_3$; $R^1$=$R^2$=$CH_3$; $R^3$=$R^5$=H; $R^6$=N($CH_3$)$_2$), a pale pink-violet colored compound which melted at 179°-181° C.

Significant infrared maxima appeared at 1305 (SO$_2$; w) and 1135 (SO$_2$; w) cm$^{-1}$. The nuclear magnetic resonance spectrum was concordant with the assigned structure.

A toluene solution of this product contacted with silica gel, acid clay or phenolic resin developed a bluish-pink colored image.

EXAMPLE 3

To a stirred mixture of 175.0 ml of ethyl alcohol, 30.35 g (0.14 mole) of 81.4 percent sodium p-toluenesulfinate, 19.5 g (0.112 mole) of 91.2 percent 1-ethyl-2-methylindole and 5.5 g (0.125 mole) of acetaldehyde under an atmosphere of nitrogen and maintaining the temperature at approximately 5° C. by means of an ice-water bath, there was added dropwise 27.5 ml of concentrated hydrochloric acid. After stirring approximately four hours at ambient temperature, the white solid which had separated was collected by filtration, washed with a small amount of ethyl alcohol and air dried to a constant weight of 43.7 g. The solid was dissolved in a hot mixture of ethyl and methyl alcohols, treated with 3.0 g of decolorizing charcoal, the solution filtered while hot, and then set aside at ambient temperature overnight. The resulting slurry was placed in a refrigerator for approximately two hours. The separated solid was then collected by filtration, washed with 500.0 ml of ethyl alcohol and air-dried to obtain 17.8 g of [(methyl)(1-ethyl-2-methyl-3-indolyl)(4-methylphenylsulfonyl)]methane (Formula X: R=4—CH$_3$; R$^1$=C$_2$H$_5$; R$^2$=CH$_3$; R$^3$=R$^4$=H; n=1), a pale yellow solid which melted at 140°-142° C. developing a purple color.

Significant infrared maxima appeared at 1290 (SO$_2$; m) and 1138 (SO$_2$; m) cm$^{-1}$.

Anal. Calcd. for C$_{20}$H$_{23}$NO$_2$S: C 70.38; H 6.75; N 4.11; S 9.38. Found: C 70.58; H 6.94; N 4.15; S 9.28.

The filtrate from the recrystallization above was concentrated to approximately 500 ml, cooled, the solid collected by filtration and dried to obtain a second crop of 9.3 g of the product which melted over the range 140°-151° C.

Significant infrared maxima appeared at 1290 (SO$_2$; m) and 1138 (SO$_2$; s) cm$^{-1}$.

An intimately ground mixture of 0.05 g of the product obtained in this example and 0.05 g of bisphenol A was slowly heated in a test tube. A color change from white to dark purple was observed as the mixture melted over the range 140°-146° C.

EXAMPLE 4

A stirred mixture of 5.0 g (0.043 mole) of indole, 1.5 g (0.05 mole) of p-formaldehyde, 7.65 g (0.043 mole) of sodium p-toluenesulfinate, 3.87 ml of glacial acetic acid and 36.6 ml of N,N-dimethylformamide was heated at approximately 150° C. for approximately four hours. The slightly cooled reaction mixture was then slowly poured with stirring into approximately 110 ml of water and 75.0 ml of chlorobenzene was added. The layers were separated after approximately twenty minutes and the water layer extracted a second time with 75.0 ml of fresh chlorobenzene and separated. The organic extracts were combined, washed with cold water and separated. A solid separated and was collected by filtration from the combined chlorobenzene layers and dried to obtain 2.18 g of [(3-indolyl)(4-methylphenylsulfonyl)]methane (Formula X: R=4—CH$_3$; R$^1$=R$^2$=R$^3$=R$^4$=H; n=0) as a white solid which melted at 152°-153° C. developing a dark purple color.

The infrared spectrum had a significant maximum at 1142 (SO$_2$; m) cm$^{-1}$. The nuclear magnetic resonance spectrum was concordant with the assigned structure.

An intimately ground mixture of this product with an equal weight of bisphenol A thermally developed a deep purple color over the range 150°-155° C.

EXAMPLE 5

To a stirred mixture at room temperature of 3.5 g (0.026 mole) of 2,5-dimethoxytetrahydrofuran, 9 g (0.05 mole) of 89 percent 1-ethyl-2-methylindole, 15 g (0.073 mole) of 86.4 percent sodium p-toluenesulfinate and 175.0 ml of ethyl alcohol, there was slowly added 15.0 ml of concentrated hydrochloric acid. The mixture was stirred at room temperature for approximately three hours and the solid that formed was collected by filtration and washed with 200.0 ml of ethyl alcohol. After drying, there was obtained 17.9 g of [α,ω-bis(1-ethyl-2-methyl-3-indolyl)-α,ω-bis(4-methylphenylsulfonyl)]butane (Formula XI: R=4—CH$_3$; R$^1$=C$_2$H$_5$; R$^2$=CH$_3$; R$^3$=H; m=2), an off-white solid which melted at 174°-175° C. developing a deep blue-black color.

In the infrared spectrum, significant maxima appeared at 1308 (SO$_2$; m) and 1142 (SO$_2$; m) cm$^{-1}$. The nuclear magnetic resonance spectrum was concordant with the assigned structure.

EXAMPLE 6

To a solution of 75.0 ml of ethyl alcohol and 39.1 g of 90 percent methanesulfonic acid, there was slowly added at room temperature with stirring 25.1 g (0.12 mole) of 85 percent sodium p-toluenesulfinate, 14.5 g (0.12 mole) of N,N-dimethylaniline and 14.9 g (1.0 mole) of p-dimethylaminobenzaldehyde. The reaction mixture was then heated with stirring at reflux temperature for approximately twenty-four hours and was then cooled to approximately 30° C. and 225.0 ml of ethyl alcohol, 70.0 ml of water and 10.0 ml of glacial acetic acid were stirred into the mixture. Then, 34.0 ml of concentrated ammonium hydroxide was slowly added allowing the temperature to rise to approximately 36° C. After cooling and stirring the mixture at approximately 5° C. for two hours, the solid which formed was collected by filtration and sequentially washed twice with 25.0 ml portions of 50 percent aqueous ethyl alcohol, three times with 100.0 ml portions of water and twice with 25.0 ml portions of 50 percent aqueous ethyl alcohol. After drying in vacuo, there was obtained 31.9 g of a light blue solid which melted over the range 140°-160° C. Twenty-five grams of the product obtained above was purified by reslurrying in 80.0 ml of ethyl alcohol at approximately 55° C. for two hours. The slurry was cooled to room temperature, the solid collected by filtration, washed twice with 25.0 ml portions of ethyl alcohol and dried to obtain 20.7 g of [bis(4-dimethylaminophenyl)(4-methylphenylsulfonyl)]methane (Formula XV: R=4—CH$_3$; R$^5$=H; R$^6$=N(CH$_3$)$_2$; Q=4-(CH$_3$)$_2$NC$_6$H$_4$), a light blue solid which melted at 173°-175° C.

The infrared spectrum had significant maxima which appeared at 1145 (SO$_2$; s) and 1302 (SO$_2$; s) cm$^{-1}$. The nuclear magnetic resonance spectrum was in accord with the assigned structure.

A toluene solution of the product contacted with an acidic clay developed a blue-colored image.

Proceeding in a manner similar to that described in Example 1 above, approximately equimolecular proportions of the appropriate aldehyde of the formula A-CHO, the appropriate 1-$R^1$-2-$R^2$-5/6-$R^3$-indole and the appropriate R-phenylsulfinic acid were interacted in ethyl alcohol in the presence of hydrochloric acid to obtain the methanes of Formulas II and V listed hereinbelow. The nuclear magentic resonance spectrum for each of the methanes listed hereinbelow was in accord with the assigned structure. A toluene solution of each product contacted with silica gel, acid clay and/or phenolic resin developed the indicated colored image.

EXAMPLE 7

Six and two-tenths grams of 80 percent sodium benzenesulfinate, 3.7 g of p-dimethylaminobenzaldehyde and 3.8 g of 94.4 percent 1-ethyl-2-methylindole were interacted at approximately 28° C. to obtain 10.7 g of a methane of Formula II wherein R=$R^3$=$R^5$=H; $R^1$=$C_2H_5$; $R^2$=$CH_3$; $R^6$=$N(CH_3)_2$, a solid which melted over the range of 148°–170° C. The infrared spectrum had a significant maxima which appeared at 1310 ($SO_2$; m) $cm^{-1}$. This product developed a red violet colored image.

EXAMPLE 8

Six and three tenths grams of 85 percent sodium p-toluenesulfinate, 2.2 g of 98 percent of N-methylpyrrole-2-carboxaldehyde and 3.8 g of 94 percent 1-ethyl-2-methylindole were interacted in 35.0 ml to obtain 8.4 g of a methane of Formula V wherein R=4—$CH_3$; $R^1$=$C_2H_5$; $R^2$=$R^8$=$CH_3$; $R^3$=H), a purple brown colored solid which melted at 180° C. A significant infrared maxima appeared at 1148 ($SO_2$; m) $cm^{-1}$ and the nuclear magnetic resonance spectrum was consistent with the assigned structure. The product developed a yellow colored image.

Following a procedure similar to that described in Example 2 above, approximately equimolecular proportions of the appropriate aldehyde of the formula A-CHO, the appropriate 1-$R^1$-2-$R^2$-5/6-$R^3$-indole and the appropriate R-phenylsulfinic acid were interacted in ethyl alcohol in the presence of hydrochloric acid to obtain the methanes of Formulas II, III, IV, VI, VII, VIII, and IX listed hereinbelow. The nuclear magnetic resonance spectrum for each of the methanes listed hereinbelow was consistent with the assigned structure. A toluene solution of each product contacted with silica gel, acid clay and/or phenolic resin developed the indicated colored image.

EXAMPLE 9

Nine and six tenths grams of 55.6 percent sodium p-toluenesulfinate, 3.4 g of anisaldehyde and 3.8 g of 86.1 percent 1-ethyl-2-methylindole were interacted to obtain 9.4 g of a methane of Formula II wherein R=4—$CH_3$; $R^1$=$C_2H_5$; $R^2$=$CH_3$; $R^3$=$R^5$=H; $R^6$=$OCH_3$, a pale orange solid which melted over the range 181°–184° C. Significant infrared maxima appeared at 1310 ($SO_2$; m) and 1140 ($SO_2$; w) $cm^{-1}$. The product developed a pale yellow colored image.

EXAMPLE 10

Six and one half grams of 81.9 percent sodium p-toluenesulfinate, 5.1 g of 95 percent 2-phenylindole and 3.8 g of p-dimethylaminobenzaldehyde were interacted to obtain 10.3 g of a methane of Formula II wherein R=4—$CH_3$; $R^1$=$R^3$=$R^5$=H; $R^2$=$C_6H_5$; $R^6$=$N(CH_3)_2$, a light brown powder melting at 185.5°–188° C. The infrared spectrum had significant maxima at 1310 ($SO_2$; m) and 1140 ($SO_2$; m) $cm^{-1}$. The product developed a violet colored image.

EXAMPLE 11

Six and one half grams of 81.9 percent sodium p-toluenesulfinate, 3.0 g of indole and 3.8 g of p-dimethylaminobenzaldehyde were interacted to obtain 2.2 g of a methane of Formula II wherein R=4—$CH_3$; $R^1$=$R^2$=$R^3$=$R^5$=H; $R^6$=$N(CH_3)_2$, a pale brown solid which melted at 167°–169° C. A significant infrared maximum appeared at 1140 ($SO_2$; m) $cm^{-1}$. The product developed a violet-pink colored image.

EXAMPLE 12

Three and seven tenths grams of 81.9 percent sodium p-toluenesulfinate, 2.1 g of 2,5-dimethylindole and 2.1 g of p-dimethylaminobenzaldehyde were interacted to obtain 6.5 g of a methane of Formula II wherein R=4—$CH_3$; $R^1$=$R^5$=H; $R^2$=$R^3$=$CH_3$; $R^6$=$N(CH_3)_2$, a solid which melted over the range 106°–112° C. In the infrared spectrum, significant maxima appeared at 1305 ($SO_2$; m) and 1145 ($SO_2$; m) $cm^{-1}$. The product developed a pink colored image.

EXAMPLE 13

Six and one half grams of 81.9 percent sodium p-toluenesulfinate, 3.6 g of 97 percent p-chlorobenzaldehyde and 3.8 g of 1-ethyl-2-methylindole were interacted to obtain 4.0 g of a methane of Formula II wherein R=4—$CH_3$; $R^1$=$C_2H_5$; $R^2$=$CH_3$; $R^3$=$R^5$=H; $R^6$=Cl, a solid which melted at 146°–149° C. Significant infrared maxima appeared at 1305 ($SO_2$; m) and 1144 ($SO_2$; b) $cm^{-1}$. The product developed a yellow colored image.

EXAMPLE 14

Six and one half grams of 81.9 percent sodium p-toluenesulfinate, 3.0 g of p-tolualdehyde and 3.8 g of 86.1 percent 1-ethyl-2-methylindole were interacted to obtain 7.7 g of a methane of Formula II wherein R=4—$CH_3$; $R^1$=$C_2H_5$; $R^2$=$R^6$=$CH_3$; $R^3$=$R^5$=H, a solid which melted at 138°–141° C. In the infrared spectrum, significant maxima appeared at 1305 ($SO_2$; m) and 1145 ($SO_2$; m) $cm^{-1}$. The product developed a yellow-green colored image.

EXAMPLE 15

Six and one half grams of 81.9 percent sodium p-toluenesulfinate, 6.3 g of 95 percent 4-(N-ethyl-N-benzyl)benzaldehyde and 3.8 g of 86.1 percent of 1-ethyl-2-methylindole were interacted to obtain 15.3 g of a methane of Formula II wherein R=4—$CH_3$; $R^1$=$C_2H_5$; $R^2$=$CH_3$; $R^3$=$R^5$=H; $R^6$=$N[(C_2H_5)(CH_2C_6H_5)]$, a gray tar-like product. A significant infrared maximum appeared at 1145 ($SO_2$; m) $cm^{-1}$. The product developed a red-violet colored image.

EXAMPLE 16

Six and one half grams of 81.9 percent sodium p-toluenesulfinate, 5.6 g of N-ethyl-3-carbazolecarboxaldehyde and 3.8 g of 86.1 percent 1-ethyl-2-methylindole were interacted to obtain 10.8 g of a methane of Formula IV wherein R=4—$CH_3$; $R^1$=$R^7$=$C_2H_5$; $R^2$=$CH_3$; $R^3$=H, a magenta colored solid which melted at 168°–171° C. A significant infrared maxima appeared at 1300 (SO$_2$; m) and 1140 (SO$_2$; m) cm$^{-1}$. The product developed a violet-pink colored image.

EXAMPLE 17

Six and one half grams of 81.9 percent sodium p-toluenesulfinate, 5.0 g of julolidinealdehyde and 3.8 g of 86.1 percent 1-ethyl-2-methylindole were interacted to obtain 12.9 g of a methane of Formula IX wherein R=4—CH$_3$; R$^1$=C$_2$H$_5$; R$^2$=CH$_3$; R$^3$=H, a blue colored solid. The infrared spectrum showed a maximum at 1145 (SO$_2$; m) cm$^{-1}$. The product developed a light purple colored image.

EXAMPLE 18

Six and one half grams of 81.9 percent sodium p-toluenesulfinate, 2.4 g of 2-furaldehyde and 3.8 g of 86.1 percent 1-ethyl-2-methylindole were interacted to obtain 4.5 g of a methane of Formula VI wherein R=4—CH$_3$; R$^1$=C$_2$H$_5$; R$^2$=CH$_3$; R$^3$=H, a black solid which melted at 144°–146° C. A significant infrared maxima appeared at 1305 (SO$_2$; m) and 1150 (SO$_2$; m) cm$^{-1}$. The product developed a yellow colored image.

EXAMPLE 19

Six and two tenths grams of 85.9 percent sodium p-toluenesulfinate, 4.5 g of 94.4 percent 1-ethyl-2-methylindole and 2.8 g of thiophene-2-carboxaldehyde were interacted to obtain 10.0 g of methane of Formula VII wherein R=4—CH$_3$; R$^1$=C$_2$H$_5$; R$^2$=CH$_3$; R$^3$=H, a white solid which melted at 168°–169° C. with decomposition. The infrared spectrum showed a significant maximum at 1140 (SO$_2$; m) cm$^{-1}$. The product developed a yellow colored image.

EXAMPLE 20

Six and four tenths grams of 85 percent sodium p-toluenesulfinate, 2.7 g of 2-pyridine carboxaldehyde and 4.2 g of 94.4 percent 1-ethyl-2-methylindole were interacted at room temperature to obtain 6.2 g of a methane of Formula VIII wherein R=4—CH$_3$; R$^1$=C$_2$H$_5$; R$^2$=CH$_3$; R$^3$=H, a slightly pink colored solid which melted at 180°–182° C. A significant infrared maximum appeared at 1140 (SO$_2$; m) cm$^{-1}$. The product slowly developed a purple-red colored image.

EXAMPLE 21

Six and one half grams of 85.9 percent sodium p-toluenesulfinate, 4.6 g of 1-ethyl-2-methylindole-3-carboxaldehyde and 3.8 g of 1-ethyl-2-methylindole were interacted to obtain 4.5 g of a methane of Formula III wherein R=4—CH$_3$; R$^1$=R$^{1'}$=C$_2$H$_5$; R$^2$=R$^{2'}$=CH$_3$; R$^3$=R$^{3'}$=H, a pink colored solid which melted over the range 146°–152° C. The infrared spectrum had significant maxima at 1305 (SO$_2$; m) and 1150 (SO$_2$; m) cm$^{-1}$. The product developed a deep orange colored image.

EXAMPLE 22

Six and one half grams of 85.9 percent sodium p-toluenesulfinate, 3.6 g of indole-3-carboxaldehyde and 4.1 g of 1-ethyl-2-methylindole were interacted at ambient temperature to obtain 5.8 g of a methane of Formula III wherein R=4—CH$_3$; R$^2$=C$_2$H$_5$; R$^1$=CH$_3$; R$^3$=R$^{1'}$=R$^{2'}$=R$^{3'}$=H, a pink colored solid which melted over the range 190°–210° C. The infrared spectrum had significant maxima at 1280 (SO$_2$; m) and 1135 (SO$_2$; m) cm$^{-1}$. The product developed a deep orange colored image.

In a manner similar to that described in Example 3 above, approximately equimolecular proportions of the appropriate aldehyde of the formula A—CHO, the appropriate 1-R$^1$-2-R$^2$-5/6-R$^3$-indole and the appropriate R-phenylsulfinic acid were interacted in ethyl alcohol in the presence of hydrochloric acid to obtain the methanes or alkanes of Formulas II, V, VI, VII, X and XI listed hereinbelow. The nuclear magnetic resonance spectrum for each of the methanes listed hereinbelow was in accord with the assigned structure.

EXAMPLE 23

Eight grams of 1,2-dimethylindole, 2.5 g of acetaldehyde and 15 g of 86.4 percent sodium p-toluenesulfinate were interacted to obtain 11.2 g of a methane of Formula X wherein R=4—CH$_3$; R$^1$=R$^2$=CH$_3$; R$^3$=R$^4$=H; n=1, a white solid which melted at 166°–167° C. developing a deep purple color. The infrared spectrum showed significant maxima at 1300 (SO$_2$; b) and 1145 (SO$_2$; m) cm$^{-1}$.

EXAMPLE 24

Ten and one half grams of 2-phenylindole, 2.5 g of acetaldehyde and 15 g of 86.4 percent sodium p-toluenesulfinate were interacted to obtain 12.6 g of a methane of Formula X wherein R=4—CH$_3$; R$^1$=R$^3$=R$^4$=H; R$^2$=C$_6$H$_5$; n=1, a gray solid which melted at 172°–174° C. with decomposition developing a blue color. Significant infrared spectrum maxima appeared at 1300 (SO$_2$; m) and 1145 (SO$_2$; m) cm$^{-1}$.

EXAMPLE 25

Thirty and thirty-five one hundredths grams of 86.4 percent sodium p-toluenesulfinate, 11.6 g of indole and 5.5 g of acetaldehyde were interacted to obtain 27.35 g of a methane of Formula X wherein R=4—CH$_3$; R$^1$=R$^2$=R$^3$=R$^4$=H; n=1, a pink-salmon colored solid which melted at 160°–162° C. developing a dark red color. The infrared spectrum showed significant maxima at 1290 (SO$_2$; m) and 1141 (SO$_2$; m) cm$^{-1}$. An intimately ground mixture of the product with an equal weight of bisphenol A thermally developed a deep red color at 160°–162° C.

EXAMPLE 26

Six and seven one hundredths grams of 86.4 percent sodium p-toluenesulfinate, 3.9 g of 91.2 percent 1-ethyl-2-methylindole and 2.85 g of heptaldehyde were interacted to obtain 4.8 g of a methane of Formula X wherein R=4—CH$_3$; R$^1$=C$_2$H$_5$; R$^2$=R$^4$=CH$_3$; R$^3$=H; n=5, an oily orange solid. Significant infrared maxima appeared at 1315 (SO$_2$; m) and 1148 (SO$_2$; m) cm$^{-1}$. The product combined with an equal weight of bisphenol A in intimately ground admixture thermally developed a deep red color.

EXAMPLE 27

Two and one half grams of glutaraldehyde, 8 g of 1-ethyl-2-methylindole and 12 g of 86.4 percent sodium p-toluenesulfinate were interacted at ambient temperature to obtain 6.5 g of a methane of Formula XI wherein R=4—CH$_3$; R$^1$=C$_2$H$_5$; R$^2$=CH$_3$; R$^3$=H; m=3, a light tan solid which, after one recrystallization from ethyl alcohol, melted at 169°–170° C. developing a deep purple color. Significant infrared maxima appeared at 1300 (SO$_2$; m) and 1145 (SO$_2$; m) cm$^{-1}$.

EXAMPLE 28

One and seven tenths grams of 2-pyridine carboxaldehyde, 2.8 g of 1-ethyl-2-methylindole and 3.0 g of 4-acetamidobenzenesulfinic acid were interacted in the absence of hydrochloric acid to obtain 5.5 g of a methane of Formula VIII wherein R=CH$_3$CONH; R$^1$=C$_2$H$_5$; R$^2$=CH$_3$; R$^3$=H, a white solid which melted at 214.8°–215.9° C. A significant infrared maximum appeared at 1320 (SO$_2$; m) cm$^{-1}$. A toluene solution of the product contacted with an acidic clay developed a yellow colored image.

EXAMPLE 29

Two and one half grams of N-methylpyrrole, 5.6 g of 1-ethyl-2-methylindole-3-carboxaldehyde and 6.0 g of sodium p-toluenesulfinate were interacted to obtain 7.1 g of a methane of Formula V wherein R=R$^3$=CH$_3$; R$^1$=C$_2$H$_5$; R$^7$=CH$_3$, a pink solid which melted at 175.5°–176.5° C. A significant infrared maximum appeared at 1302 (SO$_2$; m) cm$^{-1}$. A toluene solution of the product contacted with silica gel, an acidic clay or a phenolic resin developed a yellow colored image.

EXAMPLE 30

Five and six tenths grams of 2-thienylcarboxaldehyde, 9.2 g of 86.1 percent 1-ethyl-2-methylindole and 8.2 g of sodium benzenesulfinate were interacted to obtain 0.8 g of a methane of Formula VII R=R$^3$=H; R$^1$=C$_2$H$_5$; R$^2$=CH$_3$, a red-violet colored solid which melted at 119.5°–124° C. The infrared spectrum showed a significant maximum at 1300 (SO$_2$; m) cm$^{-1}$. A toluene solution of the product contacted with an acidic clay or silica gel developed a deep yellow colored image.

EXAMPLE 31

Four and eight tenths grams of furfural, 9.2 g of 86.1 percent 1-ethyl-2-methylindole and 8.2 g of sodium benzenesulfinate were interacted to obtain 2.1 g of a methane of Formula VI wherein R=R$^3$=H; R$^1$=C$_2$H$_5$; R$^2$=CH$_3$, a red-purple solid which melted at 123.5°–125° C. Significant infrared maxima appeared at 1300 (SO$_2$; s) and 1145 (SO$_2$; m) cm$^{-1}$. A toluene solution of the product contacted with silica gel, an acidic clay and a phenolic resin developed a yellow colored image.

EXAMPLE 32

One and one half grams of 2-thienylcarboxaldehyde, 3.0 g of 85.6 percent 1-ethyl-2-methylindole and 3.0 g of magnesium 4-chlorobenzenesulfinate were interacted to obtain 4.5 g of a methane of Formula VII wherein R=4—Cl; R$^1$=C$_2$H$_5$; R$^2$=CH$_3$; R$^3$=H, a pale pink colored solid which melted at 130°–135° C. The infrared spectrum showed a maximum at 1310 (SO$_2$; m) cm$^{-1}$. A toluene solution of the product contacted with silica gel developed a yellow colored image.

EXAMPLE 33

Two and three tenths grams of 2-thienylcarboxaldehyde, 4.3 g of 1-ethyl-2-methylindole and 3.5 g of 4-methoxybenzenesulfinic acid were interacted in methyl alcohol in the place of ethyl alcohol and in the absence of hydrochloric acid to obtain 6.5 g of a methane of Formula VII wherein R=4—OCH$_3$; R$^1$=C$_2$H$_5$; R$^2$=CH$_3$; R$^3$=H, a white solid which melted at 150°–151° C. The infrared spectrum showed a maximum at 1305 (SO$_2$; m) cm$^{-1}$. A toluene solution of the product when spotted on silica gel as an acidic clay developed a yellow colored image.

EXAMPLE 34

One and one half grams of 1,2-dimethylindole, 1.4 g of p-dimethylaminobenzaldehyde and 1.4 g of freshly prepared p-methoxybenzenesulfinic acid were interacted in the absence of hydrochloric acid at room temperature to obtain 2.0 g of a methane of Formula II wherein R=4—OCH$_3$; R$^1$=R$^2$=CH$_3$; R$^3$=R$^5$=H, R$^6$=N(CH$_3$)$_2$, a pale pink colored solid which melted at 163°–166° C. Significant infrared maxima appeared at 1305 (SO$_2$; w) and 1300 (SO$_2$; w) cm$^{-1}$. A toluene solution of this product contacted with silica gel, acid clay or phenolic resin developed a bluish-red colored image.

Proceeding in a manner similar to that described in Example 4 above, approximately equimolecular proportions of the appropriate aldehyde of the formula A—CHO, the appropriate 1-R$^1$-2-R$^2$-5/6-R$^3$-indole and the appropriate R-phenylsulfinic acid were interacted in ethyl alcohol in the presence of hydrochloric acid to obtain the methanes of Formulas II and VII listed hereinbelow. The nuclear magnetic resonance spectrum for each of the methanes listed hereinbelow was consistent with the assigned structure. A toluene solution of each product contacted with silica gel, an acidic clay and/or a phenolic resin developed the indicated colored image.

EXAMPLE 35

One and eight tenths grams of p-diethylaminobenzaldehyde, 1.8 g of 85.6 percent 1-ethyl-2-methylindole and 2.0 g of magnesium p-chlorobenzene sulfinate were interacted to obtain 4.5 g of a methane of Formula II wherein R=4—Cl; R$^1$=C$_2$H$_5$; R$^2$=CH$_3$; R$^3$=R$^5$=H; R$^6$=N(C$_2$H$_5$)$_2$, a pink oil. In the infrared spectrum, a maximum appeared at 1270 (SO$_2$; m) cm$^{-1}$. The product developed a red colored image.

EXAMPLE 36

Two and three tenths grams of p-dimethylaminobenzaldehyde, 2.8 g of 85.6 percent 1-ethyl-2-methylindole and 5.0 g of sodium p-dodecylbenzenesulfinate were interacted to obtain after extraction with toluene followed by extraction with isopropanol 0.7 g of a methane of Formula II wherein R=4—C$_{12}$H$_{25}$; R$^1$=C$_2$H$_5$; R$^2$=CH$_3$; R$^3$=R$^5$=H; R$^6$=N(CH$_3$)$_2$, an oily solid. The nuclear magnetic resonance spectrum was concordant with the assigned structure. The product developed a blue-red colored image.

EXAMPLE 37

Two and one half grams of 2-thienylcarboxaldehyde, 3.0 g of 1-ethyl-2-methylindole and 5.0 g of sodium p-dodecylbenzenesulfinate were interacted to obtain, after extracting with toluene, 2.3 g of a methane of Formula VII wherein R=4—C$_{12}$H$_{25}$; R$^1$=C$_2$H$_5$; R$^2$=CH$_3$; R$^3$=H, an oily solid which melted over the range 152.8°–162.5° C. The infrared spectrum had a significant maximum at 1180 (SO$_2$; m) cm$^{-1}$. The product developed a yellow colored image.

Following a procedure similar to that described in Example 6 above, approximately equimolecular proportions of the appropriate 2-R$^5$-4-R$^6$-benzaldehyde, the appropriate compound of the formula Q-H and the appropriate R-phenylsulfinic acid were interacted in ethyl alcohol to obtain the methanes of Formulas II and XV listed hereinbelow. The nuclear magnetic resonance spectrum for each of the methanes listed hereinbelow was concordant with the assigned structure. A toluene solution of each product contacted with silica gel, an acidic clay and/or a phenolic resin developed the indicated colored image.

EXAMPLE 38

Twenty and six tenths grams of 86.4 percent sodium p-toluenesulfinate, 21.3 g of 99.2 percent N-ethyl-N-benzylaniline and 14.9 g of p-dimethylaminobenzaldehyde were interacted in the presence of 36.4 g of 95 percent methanesulfonic acid to obtain 28.7 g of a methane of Formula XV wherein $R=4-CH_3$; $R^5=H$; $R^6=N(CH_3)_2$; $Q=4-[(C_2H_5)(C_6H_5CH_2)]NC_6H_4$, a bluish-gray solid which melted over the range 166°–172° C. A significant infrared maximum appeared at 1148 ($SO_2$; m) cm$^{-1}$. The product developed a blue colored image.

EXAMPLE 39

Twenty and six tenths grams of 86.4 percent sodium p-toluenesulfinate, 21.3 g of 90 percent N,N-diethyl-3-ethoxyaniline and 14.9 g of 4-dimethylaminobenzaldehyde were interacted in the presence of 36.4 g of 95 percent methanesulfonic acid to obtain 5.4 g of a methane of Formula XV wherein $R=4-CH_3$; $R^5=C_2H_5O$; $R^6=N(C_2H_5)_2$; $Q=4-(CH_3)_2NC_6H_4$, a light tan colored solid which melted at 130°–132° C. The infrared spectrum had a significant maximum at 1144 ($SO_2$; m) cm$^{-1}$. The product developed a blue-violet colored image.

EXAMPLE 40

Ten and three tenths grams of 86.4 percent sodium p-toluenesulfinate, 10.7 g of 90.7 percent N,N-diethyl-3-ethoxyaniline and 12 g of 4-(N-ethyl-N-benzyl)-aminobenzaldehyde were interacted in the presence of 18.2 g of 95 percent methanesulfonic acid to obtain a methane of Formula XV wherein $R=4-CH_3$; $R^5=C_2H_5O$; $R^6=N(C_2H_5)_2$; $Q=4-[(C_2H_5)(C_6H_5CH_2)NC_6H_4]$, an oil. A significant infrared maximum appeared at 1145 ($SO_2$; s) cm$^{-1}$. The product developed a violet colored image.

EXAMPLE 41

Fourteen and nine tenths grams of 4-dimethylaminobenzaldehyde, 20.6 g of 86.4 percent sodium p-toluenesulfinate and 16.0 g of N,N-diethyl-3-methylaniline were interacted in the presence of 36.4 g of 95 percent methanesulfonic acid to obtain 0.82 g of a methane of Formula XV wherein $R=4-CH_3$; $R^5=CH_3$; $R^6=N(C_2H_5)_2$; $Q=4-(CH_3)_2NC_6H_4$, a dark brown oil. The infrared spectrum had a significant maximum at 1147 ($SO_2$; m) cm$^{-1}$. The product developed a blue colored image.

EXAMPLE 42

Fourteen and nine tenths grams of 4-dimethylaminobenzaldehyde, 20.7 g of 85.9 percent sodium p-toluenesulfinate and 14.7 g of N,N-diethylaniline were interacted in 100.0 ml of isopropyl alcohol in place of ethyl alcohol and in the presence of 29.0 ml of concentrated hydrochloric acid to obtain 0.82 g of a methane of Formula XV wherein $R=4-CH_3$; $R^5=H$; $R^6=N(CH_3)_2$; $Q=4-(C_2H_5)_2NC_6H_4$, a gray solid which melted over the range 108°–150° C. The infrared spectrum had a significant maximum at 1143 ($SO_2$; m) cm$^{-1}$. The product developed a blue colored image.

EXAMPLE 43

Eighteen and six tenths grams of 95.8 percent sodium p-toluenesulfinate, 12.1 g of N,N-dimethylaniline and 18.6 g of 2-chloro-4-dimethylaminobenzaldehyde were interacted in the presence of 36.4 g of 95 percent methanesulfonic acid to obtain 2.7 g of a methane of Formula XV wherein $R=4-CH_3$; $R^5=Cl$; $R^6=N(CH_3)_2$; $Q=4-(CH_3)_2NC_6H_4$, pink colored solid which melted over the range 130.5°–146° C. Significant infrared maxima appeared at 1150 ($SO_2$; s) and 1305 ($SO_2$; m) cm$^{-1}$. The product developed a blue colored image.

EXAMPLE 44

Twenty and six tenths grams of 86.4 percent sodium p-toluenesulfinate, 21.3 g of 3-ethoxy-N,N-diethylaniline and 13.6 g of p-anisaldehyde were interacted in the presence of 36.4 g of 95 percent methanesulfonic acid to obtain 13.8 g of a methane of Formula XV wherein $R=4-CH_3$; $R^5=H$; $R^6=OCH_3$; $Q=2-C_2H_5O-4-(C_2H_5)_2NC_6H_3$, an off-white colored solid which melted at 117.2°–117.8° C. The infrared spectrum showed significant maxima at 1151 ($SO_2$; s) and 1304 ($SO_2$; s) cm$^{-1}$. The product developed a yellow colored image.

EXAMPLE 45

Twenty and six tenths grams of 86.4 percent sodium p-toluenesulfinate, 21.3 g of 90.7 percent N,N-diethyl-m-phenetidine and 12.0 g of 4-methylbenzaldehyde were interacted in the presence of 36.4 g of 95 percent methanesulfonic acid to obtain 23.9 g of a methane of Formula XV wherein $R=4-CH_3$; $R^5=H$; $R^6=CH_3$; $Q=2-C_2H_5O-4-(C_2H_5)_2NC_6H_3$, a white solid which melted at 108.4°–109.8° C. Significant infrared maxima appeared at 1143 ($SO_2$; s) and 1303 ($SO_2$; m) cm$^{-1}$. The product developed a yellow colored image.

EXAMPLE 46

Eighteen and six tenths grams of 95.8 percent sodium p-toluenesulfinate, 14.9 g of 4-dimethylaminobenzaldehyde and 17.7 g of 98 percent julolidine were interacted in the presence of 29.5 ml of 37.9 percent hydrochloric acid to obtain 15.0 g of a methane of Formula XV wherein $R=4-CH_3$; $R^5=H$; $R^6=N(CH_3)_2$; $Q=9$-julolidinyl, a white solid which melted over the range 129.1°–134.4° C. The infrared spectrum showed significant maxima at 1140 ($SO_2$; s) and 1305 ($SO_2$; m) cm$^{-1}$.

EXAMPLE 47

Four and seven tenths grams of p-dimethylaminobenzaldehyde, 5.5 g of 1-ethyl-2-methylindole and 8.0 g of 75 percent 4-acetamidobenzenesulfinic acid were interacted to obtain after reslurrying in isopropanol and filtering, 6.3 g of a methane of Formula II wherein $R=4-NHCOCH_3$; $R^1=C_2H_5$; $R^2=CH_3$; $R^3=R^5=H$; $R^6=N(CH_3)_2$, a solid which melted over the range 145°–157° C. The infrared spectrum showed a maximum at 1165 ($SO_2$; m) cm$^{-1}$. The product developed a yellow-green colored image.

EXAMPLE 48

Fourteen and eight tenths grams of 99.4 percent N-ethyl-N-benzylaniline, 10.4 g of p-dimethylaminobenzaldehyde and 11.4 g of sodium benzenesulfinate were interacted in the presence of 26.0 g of methanesulfonic acid to obtain 1.3 g of a methane of Formula XV wherein $R=R^5=H$; $R^6=N(CH_3)_2$; $Q=4-[(C_2H_5)-(C_6H_5CH_2)]NC_6H_4$, which melted over the range 111°–118° C. A significant infrared maximum appeared at 1300 ($SO_2$; m) $cm^{-1}$. The product developed a blue colored image.

Proceeding in a manner similar to that described in Example 6 above, approximately equimolecular proportions of 1-methylpyrrole, the appropriate aldehyde of the formula Z-CHO and the appropriate R-phenylsulfinic acid were interacted in ethyl alcohol in the presence of hydrochloric acid to obtain the methanes of Formula XVI listed hereinbelow. The nuclear magnetic resonance spectrum for each of the methanes listed hereinbelow was in accord with the assigned structure. A toluene solution of each product contacted with silica gel and/or an acidic clay developed the indicated colored image.

EXAMPLE 49

Four and two tenths grams of 4-chlorobenzaldehyde, 2.4 g of 1-methylpyrrole and 6.0 g of sodium p-toluenesulfinate were interacted to obtain 7.3 g of a methane of Formula XVII wherein $R=4-CH_3$; $R^8=CH_3$; $R^5=H$; $R^6=Cl$, a solid which melted at 122° C. with decomposition. The infrared spectrum had a significant maximum at 1305 ($SO_2$; m) $cm^{-1}$. The product developed a yellow colored image.

EXAMPLE 50

Six grams of 4-methylbenzaldehyde, 4.2 ml of 1-methylpyrrole and 9.5 g of sodium p-toluenesulfinate were interacted to obtain 17.1 g of a methane of Formula XVII wherein $R=4-CH_3$; $R^6=R^8=CH_3$; $R^5=H$, a pink colored solid which melted at 78° C. with decomposition. The infrared spectrum had a significant maximum at 1305 ($SO_2$; m) $cm^{-1}$. The product developed a yellow color.

EXAMPLE 51

Seven and four tenths grams of 4-methoxybenzaldehyde, 4.5 g of 1-methylpyrrole and 10.0 g of sodium benzenesulfinate were interacted to obtain 12.0 g of a methane of Formula XVII wherein $R=R^5=H$; $R^6=CH_3O$; $R^8=CH_3$, a pink colored solid which melted at 103.5°–105° C. The infrared spectrum had a significant maximum at 1305 ($SO_2$; m) $cm^{-1}$. The product developed a yellow colored image.

EXAMPLE 52

Thirty-seven grams of 4-methoxybenzaldehyde, 44.5 g of p-toluenesulfinate and 22.5 g of 1-methylpyrrole were interacted to obtain after extraction with 10 percent diethanolamine in isopropyl alcohol 57.8 g of a methane of Formula XVII wherein $R=4-CH_3$; $R^8=CH_3$; $R^5=H$; $R^6=CH_3O$, a solid. The infrared spectrum had a significant maximum at 1307 ($SO_2$; m) $cm^{-1}$. The product developed a yellow colored image.

EXAMPLE 53

Six and one half grams of 4-acetamidobenzenesulfinic acid, 2.5 g of 1-methylpyrrol and 3.4 g of 2-thiophenecarboxaldehyde were interacted to obtain 3.2 g of a methane of Formula XVIII wherein $R=4-NHCOCH_3$; $R^8=CH_3$, a rust colored solid which melted over the range 130°–145° C. The infrared spectrum had a significant maximum at 1305 ($SO_2$; m) $cm^{-1}$. The product developed a pink colored image.

EXAMPLE 54

Seven grams of sodium benzenesulfinate, 3.4 g of 2-thiophenecarboxaldehyde and 2.5 g of 1-methylpyrrole were interacted to obtain 3.0 g of a methane of Formula XVIII wherein $R=H$; $R^8=CH_3$, a pink colored solid which melted at 100°–102° C. The infrared spectrum had a significant maximum at 1300 ($SO_2$; m) $cm^{-1}$. The product developed a yellow colored image.

EXAMPLE 55

Six grams of 98.5 percent sodium p-toluenesulfinate, 3.4 g of 2-thiophenecarboxaldehyde and 2.5 g of 1-methylpyrrole were interacted to obtain after washing with 5 percent diethanolamine in isopropyl alcohol 2.4 g of a methane of Formula XVIII wherein $R=4-CH_3$; $R^8=CH_3$, a pink-white colored solid which melted at 118° C. with decomposition. The infrared spectrum had a significant maximum at 1305 ($SO_2$; m) $cm^{-1}$. The product developed a yellow colored image.

EXAMPLE 56

Nineteen grams of sodium p-toluenesulfinate, 9.6 g of 2-furaldehyde and 8.5 g of 1-methylpyrrole were interacted to obtain 21.0 g of a methane of Formula XIX wherein $R=4-CH_3$; $R^8=CH_3$, a light gray colored solid which melted over the range 95°–100° C. The infrared spectrum had a significant maximum at 1300 ($SO_2$; m) $cm^{-1}$. The product developed a yellow colored image.

EXAMPLE 57

Two grams of sodim p-toluenesulfinate, 2.4 g of N-ethyl-3-carbazolecarboxaldehyde and 0.9 g of 1-methylpyrrole were interacted to obtain 3.0 g of a methane of Formula XX wherein $R=4-CH_3$; $R^7=C_2H_5$; $R^8=CH_3$, a pale grape colored solid which melted over the range 82°–87° C. The infrared spectrum had a significant maximum at 1305 ($SO_2$; m) $cm^{-1}$. The product developed a grape colored image.

Proceeding in a manner similar to that described in Example 1 above substituting for ethyl alcohol and the concentrated hydrochloric acid the appropriate reaction medium and the appropriate catalyst listed in Examples 58–82 of Table A hereinbelow, 4-dimethylaminobenzaldehyde, sodium p-toluenesulfinate and 1-ethyl-2-methylindole were interacted at the indicated temperature to obtain a methane of Formula II wherein $R=4-CH_3$; $R^1=C_2H_5$; $R^2=CH_3$; $R^3=R^5=H$; $R^6=N(CH_3)_2$. A toluene or acetone solution of the product from Examples 58–82 contacted with silica gel developed a blue-red colored image.

TABLE A

| Example | Reaction Medium | Catalyst | Reaction Temperature |
|---|---|---|---|
| 58 | ethylene dichloride | p-toluenesulfonic acid | 25° C. |
| 59 | diethylene glycol dimethyl ether | acetic acid | 25° C. |
| 60 | ethyl alcohol | phosphoric acid | 10°–25° C. |
| 61 | ethylene glycol monoethyl ether | phosphoric acid | −10° C. |
| 62 | chlorobenzene | aluminum chloride | reflux |
| 63 | toluene | zinc chloride | 25° C. |
| 64 | ethylene dichloride | stannic chloride | 25° C. |
| 65 | ethylene dichloride | thionyl chloride | 25° C. |
| 66 | chlorobenzene | benzoyl peroxide | reflux |
| 67 | 1-ethyl-2-methylindole | stannic chloride | 20°–30° C. |
| 68 | ethyl alcohol | hydrobromic acid | RT |

TABLE A-continued

| Example | Reaction Medium | Catalyst | Reaction Temperature |
|---|---|---|---|
| 69 | ethyl alcohol | fluoroboric acid | RT |
| 70 | ethyl alcohol | hydriodic acid | RT |
| 71 | ethyl alcohol | nitric acid | RT |
| 72 | ethyl alcohol | perchloric acid | RT |
| 73 | ethyl alcohol | formic acid | RT |
| 74 | ethyl alcohol | trifluoroacetic acid | RT |
| 75 | ethyl alcohol | glycolic acid | RT |
| 76 | ethyl alcohol | malonic acid | RT |
| 77 | ethyl alcohol | fumaric acid | RT |
| 78 | ethyl alcohol | benzoic acid | RT |
| 79 | ethyl alcohol | citric acid | RT |
| 80 | ethyl alcohol | salicylic acid | RT |
| 81 | ethyl alcohol | picric acid | RT |
| 82 | ethyl alcohol | trimellitic acid | RT |

Following a procedure similar to that described in Example 6 above substituting for ethyl alcohol and methanesulfonic acid the appropriate reaction medium and the appropriate catalyst listed in Examples 83–109 of Table B hereinbelow, 4-dimethylaminobenzaldehyde, N,N-dimethylaniline and sodium p-toluenesulfinate were interacted at the indicated temperature to obtain a methane of Formula XV wherein R=4—$CH_3$; $R^5$=H, $R^6$=N($CH_3$)$_2$; Q=4—($CH_3$)$_2$N$C_6H_4$. A toluene or acetone solution of the product from Examples 83-109 contacted with silica gel developed a blue colored image.

TABLE B

| Example | Reaction Medium | Catalyst | Reaction Temperature |
|---|---|---|---|
| 83 | isopropyl alcohol | p-toluenesulfonic acid | 80° C. |
| 84 | acetonitrile | p-toluenesulfonic acid | reflux |
| 85 | ethylene dichloride | p-toluenesulfonic acid | 70°–75° C. |
| 86 | ethyl alcohol | sulfuric acid | reflux |
| 87 | water | sulfuric acid | 90° C. |
| 88 | isopropyl alcohol | sulfuric acid | reflux |
| 89 | water | methanesulfonic acid | 85°–90° C. |
| 90 | ethyl alcohol | hydrochloric acid | reflux |
| 91 | isopropyl alcohol | hydrochloric acid | reflux |
| 92 | water | hydrochloric acid | reflux |
| 93 | ethyl alcohol | phosphoric acid | reflux |
| 94 | ethylene dichloride | phosphorus trichloride | 25° C. |
| 95 | ethylene dichloride | phosphorus pentachloride | 25°–30° C. |
| 96 | N,N-dimethylformamide & isopropyl alcohol | phosphorus oxychloride | 45°–50° C. |
| 97 | acetonitrile | phosphorus oxychloride | reflux |
| 98 | ethylene dichloride | thionyl chloride | 25° C. |
| 99 | ethylene dichloride | boron trifluoride etherate | reflux |
| 100 | N,N-dimethylaniline | boron trifluoride etherate | reflux |
| 101 | ethylene dichloride | ferric chloride | reflux |
| 102 | ethylene dichloride | ferric oxide | reflux |
| 103 | ethylene dichloride | aluminum oxide | reflux |
| 104 | ethylene dichloride | p-toluenesulfonic acid | reflux |
| 105 | acetonitrile | benzoyl chloride | reflux |
| 106 | acetonitrile | phosphorus pentaoxide | 20°–60° C. |
| 107 | isopropyl crown ether | potassium fluoride | reflux |
| 108 | chlorobenzene | p-toluenesulfonic acid | 80°–90° C. |
| 109 | N,N-dimethylaniline | thionyl chloride | 25°–30° C. |

It is contemplated that by following procedures similar to those described in the foregoing examples but employing the appropriate 2-$R^5$-4-$R^6$-benzaldehyde, the appropriate 1-$R^1$-2-$R^2$-5/6-$R^3$-indole and the appropriate R-phenylsulfinic acid, there will be obtained the [(2-$R^5$-4-$R^6$-phenyl)(1-$R^1$-2-$R^2$-5/6-$R^3$-3-indolyl)(R-phenylsulfonyl)]methanes of Formula II, Examples 110-120, presented in Table C hereinbelow.

TABLE C

| | | Methanes of Formula II | | | | |
|---|---|---|---|---|---|---|
| Ex. | R | $R^1$ | $R^2$ | $R^3$ | $R^5$ | $R^6$ |
| 110 | 4-Br | 2-($C_2H_5$)$C_6H_{12}$ | $CH_3$ | H | $CH_3O$ | N($CH_3$)$_2$ |
| 111 | 2,4($CH_3$)$_2$ | 4-Cl—$C_6H_4CH_2$ | $CH_3$ | 5-$NO_2$ | Cl | N($CH_3$)$_2$ |
| 112 | 2-$NO_2$ | n-$C_8H_{17}$ | $CH_3$ | H | $CH_3$ | N($C_2H_5$)$_2$ |
| 113 | 3,4($Cl$)$_2$ | $CH_3$ | H | 5-Br-6-$NO_2$ | H | i-$C_3H_7$ |
| 114 | 4-F | 2-$CH_3$—$C_6H_4CH_2$ | $CH_3$ | H | $CH_3O$ | $CH_3O$ |
| 115 | 4-$CH_3O$ | H | $C_2H_5$ | 6-$CH_3$ | $CH_3$ | N($CH_3$) ($C_6H_5CH_2$) |
| 116 | 4-Cl,3$NO_2$ | i-$C_4H_9$ | $CH_3$ | H | Br | H |
| 117 | 4-$CH_3CONH$ | 1-($CH_3$) ($C_6H_{12}$) | H | 5-I | H | $C_2H_5O$ |
| 118 | 3-$NO_2$ | $C_2H_4$ | $CH_3$ | H | $C_2H_5O$ | H |
| 119 | 2,5-($CH_3$)$_2$ | i-$C_5H_{11}$ | H | H | F | H |
| 120 | 4-I | H | i-$C_3H_7$ | H | H | NH$C_6H_5CH_2$ |

It is contemplated that by following procedures similar to those described in the foregoing examples but employing the appropriate 1-$R^{1'}$-2-$R^{2'}$-5/6-$R^{3'}$-indole-3-carboxaldehyde, the appropriate 1-$R^1$-2-$R^2$-5/6-$R^3$-indole and the appropriate R-phenylsulfinic acid, there will be obtained the [(1-$R^{1'}$-2-$R^{2'}$-5/6-$R^{3'}$-3-indolyl)(1-$R^1$-2-$R^2$-5/6-$R^3$-3-indolyl)(R-phenylsulfonyl)]methanes of Formula III, Examples 121-131, presented in Table D hereinbelow.

TABLE D

| | | | Methanes of Formula III | | | | |
|---|---|---|---|---|---|---|---|
| Ex. | R | $R^1$ | $R^2$ | $R^3$ | $R^{1'}$ | $R^{2'}$ | $R^{3'}$ |
| 121 | 4-Cl | $C_6H_5CH_2$ | H | 6-F | H | H | 5-$CH_3O$ |
| 122 | 4-$NO_2$ | H | $C_2H_5$ | 5-$CH_3$ | n-$C_8H_{17}$ | $CH_3$ | H |
| 123 | 2,4-($CH_3$)$_2$ | $CH_2CHCH_2$ | $CH_3$ | H | n-$C_4H_9$ | $C_6H_5$ | H |
| 124 | 2,5-($Cl$)$_2$ | i-$C_3H_7$ | H | H | $CH_3$ | $CH_3$ | H |
| 125 | 4-$CH_3O$ | H | $CH_3$ | 5,6-($CH_3$)$_2$ | H | H | H |
| 126 | 4-I | 4-Br$C_6H_4CH_2$ | i-$C_3H_7$ | H | $C_2H_5$ | $C_6H_5$ | H |

TABLE D-continued

| | | | Methanes of Formula III | | | | |
|---|---|---|---|---|---|---|---|
| Ex. | R | $R^1$ | $R^2$ | $R^3$ | $R^{1'}$ | $R^{2'}$ | $R^{3'}$ |
| 127 | 2,4-$(NO_2)_2$ | H | $C_6H_5$ | 5,6-$(Cl)_2$ | $C_2H_5$ | $CH_3$ | H |
| 128 | $C_2H_5$ | n-$C_4H_9$ | H | $CH_3O$ | $C_2H_5$ | $C_6H_5$ | H |
| 129 | H | $C_8H_{17}$ | $CH_3$ | H | $CH_2C_6H_5$ | H | 5-F |
| 130 | $CH_3$ | $C_4H_9$ | $CH_3$ | H | H | H | 5,6-$(CH_3O)_2$ |
| 131 | 4-Cl | H | $C_3H_7$ | H | 1-[$(CH_3)(C_6H_{12})$] | H | 5-I |

It is comtemplated that by following procedures similar to those described in the foregoing examples but employing an appropriate 9-$R^7$-3-carbazolecarboxaldehyde or 1-$R^8$-pyrrole-2-carboxaldehyde, the appropriate R-phenylsulfinic acid and the appropriate 1-$R^1$-2-$R^2$-5/6-$R^3$-indole, there will be obtained the [(9-$R^7$-3-carbazolyl)(1-$R^1$-2-$R^2$-5/6-$R^3$-3-indolyl)(R-phenylsulfonyl)]methanes of Formula IV and [(1-$R^8$-2-pyrrolyl)(1-$R^1$-2-$R^2$-5/6-$R^3$-3-indolyl)(R-phenylsulfonyl)]methanes of Formula V, Examples 132–141, presented in Table E hereinbelow.

TABLE E

| | | Methanes of Formulas IV and V | | | | | |
|---|---|---|---|---|---|---|---|
| Ex. | | R | $R^1$ | $R^2$ | $R^3$ | $R^7$ | $R^8$ |
| 132 | (IV) | H | H | $C_2H_5$ | H | $CH_3$ | — |
| 133 | (V) | 4-Cl | $C_4H_9$ | H | 5-$CH_3O$ | — | $C_6H_5$ |
| 134 | (IV) | 4-$NO_2$ | $CH_3$ | H | 6-$NO_2$ | $C_3H_7$ | — |
| 135 | (V) | 4-$CH_3O$ | 2,6-$(Cl)_2C_6H_3CH_2$ | $CH_3$ | H | — | $C_2H_5$ |
| 136 | (IV) | 4-Br | H | $C_6H_5$ | 5,6-$(Cl)_2$ | $C_6H_5$ | — |
| 137 | (V) | 2,4-$(CH_3)_2$ | 3-(2-$CH_3$)$C_3H_4$ | $CH_3O$ | H | — | $CH_3$ |
| 138 | (IV) | 4-$CH_3O$ | $C_6H_{13}$ | H | H | $C_2H_5$ | — |
| 139 | (IV) | 2-$NO_2$ | H | $CH_3$ | 6-Br | — | $C_3H_7$ |
| 140 | (V) | 2,5-$(CH_3)_2$ | $C_6H_5CH_2$ | $CH_3$ | H | H | — |
| 141 | (IV) | 3,4-$(Cl)_2$ | $CH_3$ | $CH_3$ | 6-$NO_2$ | — | H |

It is contemplated that by following procedures similar to those described in the foregoing examples but employing the appropriate 1-$R^1$-2-$R^2$-5/6-$R^3$-indole, the appropriate R-phenylsulfinic acid and the appropriate aldehyde of the formula A-CHO, there will be obtained the [(A)(1-$R^1$-2-$R^2$-5/6-$R^3$-3-indolyl)(R-phenylsulfonyl)]methanes of Formulas VI-X, Examples 142–160, presented in Table F hereinbelow.

TABLE F

| | | Methanes of Formulas VI–118 | | | | |
|---|---|---|---|---|---|---|
| Ex. | | A | R | $R^1$ | $R^2$ | $R^3$ |
| 142 | (VI) |  | 4-I | n-$C_4H_9$ | $CH_3$ | H |
| 143 | " | " | 3-$NO_2$ | 2,5-$(CH_3)_2C_6H_3CH_2$ | $CH_3$ | H |
| 144 | " | " | 4-$CH_3O$ | $CH_3$ | $CH_3$ | 6-$NO_2$ |
| 145 | " | " | 2,4-$(Cl)_2$ | i-$C_5H_{11}$ | H | H |
| 146 | " | " | 2,5-$(CH_3)_2$ | H | $C_6H_5$ | 5,6-$(Cl)_2$ |
| 147 | (VII) |  | 2-$NO_2$ | i-$C_3H_7$ | $CH_3$ | H |
| 148 | " | " | 4-Br | 3-$ClC_6H_4CH_2$ | $C_2H_5$ | H |
| 149 | " | " | 4-$CH_3CONH$ | H | H | 5,6-$(CH_3O)_2$ |
| 150 | " | " | 2,4-$(CH_3)_2$ | $CH_3$ | H | 5-Br-6-$NO_2$ |
| 151 | " | " | 4-$CH_3O$ | H | $C_2H_5$ | 5-$CH_3$ |
| 152 | (VIII) |  | 3,4-$(Cl)_2$ | $C_6H_5CH_2$ | H | 5-F |
| 153 | " |  | 4-F | s-$C_4H_9$ | $CH_3$ | H |
| 154 | " |  | 2-$NO_2$ | $C_2H_4$ | $CH_3$ | H |
| 155 | " | " | 2,5-$(CH_3)_2$ | $CH_3$ | $CH_3$ | 6-$NO_2$ |
| 156 | " |  | 4-$CH_3O$ | $C_8H_{17}$ | $CH_3$ | H |

TABLE F-continued

Methanes of Formulas VI-118

| Ex. | A | R | $R^1$ | $R^2$ | $R^3$ |
|---|---|---|---|---|---|
| 157 | (IX) | 4-Cl-3-$NO_2$ | H | $C_2H_5$ | 6-$CH_3$ |
| 158 | " | 4-Br | $C_6H_{13}$ | $CH_3$ | H |
| 159 | " | 3-$NO_2$ | 4-Br$C_6H_4CH_2$ | i-$C_3H_7$ | H |
| 160 | " | 4-$CH_3O$ | $CH_3$ | H | 6-$NO_2$ |

It is contemplated that by following procedures similar to those described in the foregoing examples but employing the appropriate $R^4(CH_2)_nCHO$, the appropriate 1-$R^1$-2-$R^2$-5/6-$R^3$-indole and the appropriate R-phenylsulfinic acid, there will be obtained the {[$R^4(CH_2)_n$](1-$R^1$-2-$R^2$-5/6-$R^3$-3-indolyl)(R-phenylsulfonyl)} methanes of Formula X, Examples 161–170, presented in Table G hereinbelow.

TABLE G

Methanes of Formula X

| Ex. | R | $R^1$ | $R^2$ | $R^3$ | $R^4$ | n |
|---|---|---|---|---|---|---|
| 161 | 4-$CH_3$ | n-$C_4H_9$ | $CH_3$ | H | $CH_3$ | 0 |
| 162 | 4-Br | H | $C_6H_5$ | H | $CH_3$ | 2 |
| 163 | 2,4-($CH_3$)$_2$ | $C_6H_5CH_2$ | H | 5-F | $CH_3$ | 8 |
| 164 | 2-$NO_2$ | $CH_3$ | H | 6-$NO_2$ | $CH_3$ | 4 |
| 165 | 4-$CH_3CONH$ | $C_8H_{17}$ | $CH_3$ | H | $CH_3$ | 5 |
| 166 | 4-Cl | $CH_3$ | $C_2H_5$ | H | $CH_3$ | 6 |
| 167 | 4-$CH_3O$ | $CH_3$ | H | 5-Br-6-$NO_2$ | $CH_3$ | 1 |
| 168 | H | $C_2H_4$ | $CH_3$ | H | $CH_3$ | 3 |
| 169 | 2,5(Cl)$_2$ | H | H | 5,6($CH_3O$)$_2$ | $CH_3$ | 7 |
| 170 | 3-$NO_2$ | i-$C_5H_{11}$ | $CH_3$ | H | $CH_3$ | 2 |

It is contemplated that by following procedures similar to those described in the foregoing examples but employing the appropriate $(CH_2)_m(CHO)_2$ or 2,5-dimethoxytetrahydrofuran for those products in which m=2, the appropriate 1-$R^1$-2-$R^2$-5/6-$R^3$-indole and the appropriate R-phenylsulfinic acid, there will be obtained the [α,ω-bis(1-$R^1$-2-$R^2$-5/6-$R^3$-3-indolyl)-α,ω-bis(R-phenylsulfonyl)]alkanes of Formula XI, Examples 171–180, presented in Table H hereinbelow.

TABLE H

Alkanes of Formula XI

| Ex. | R | $R^1$ | $R^2$ | $R^3$ | m |
|---|---|---|---|---|---|
| 171 | 4-$CH_3$ | H | H | H | 2 |
| 172 | 4-$CH_3O$ | $C_8H_{17}$ | $CH_3$ | H | 2 |
| 173 | 2-$NO_2$ | H | i-$C_3H_7$ | H | 3 |
| 174 | 3,4-(Cl)$_2$ | 2,5-($CH_3$)$_2C_6H_3CH_2$ | $CH_3$ | H | 2 |
| 175 | 4-I | H | $C_2H_5$ | 6-$CH_3$ | 3 |
| 176 | H | 1-$CH_3C_6H_{12}$ | | 5-I | 3 |
| 177 | 4-$CH_3CONH$ | H | $C_6H_5$ | 6-Cl | 2 |
| 178 | 2,5-($CH_3$)$_2$ | $CH_3$ | H | 5-Br-6-$NO_2$ | 3 |
| 179 | 4-Br | n-$C_4H_9$ | $CH_3$ | H | 3 |
| 180 | 3-$NO_2$ | $C_2H_4$ | $CH_3$ | H | 2 |

It is contemplated that by following procedures similar to those described in the foregoing examples but employing the appropriate 2-$R^5$-4-$R^6$-benzaldehyde, the appropriate compound of the formula Q-H and the appropriate R-phenylsulfinic acid, there will be obtained the [(Q)(2-$R^5$-4-$R^6$-phenyl)(R-phenylsulfonyl]methanes of Formula XV, Examples 181–198, presented in Table I hereinbelow.

TABLE I

Methanes of Formula XV

| Ex. | Q | R | $R^5$ | $R^6$ |
|---|---|---|---|---|
| 181 | 2,4-bis[($CH_3$)$_2$N]$C_6H_3$ | 4-$CH_3$ | Cl | H |
| 182 | 4-($C_3H_7$)$_2NC_6H_4$ | 4-Cl | H | $CH_3O$ |
| 183 | 3-$CH_3$—4-($CR_3$)$_2NC_6H_3$ | 2-$NO_2$ | $C_2H_5O$ | H |
| 184 | 3-$CH_3O$-4-($C_2H_5$)$_2NC_6H_3$ | H | $CH_3O$ | $CH_3O$ |
| 185 | 9-julolidinyl | 2,5-($CH_3$)$_2$ | Cl | N($CH_3$)$_2$ |
| 186 | 2-$C_2H_5O$—4-($C_2H_5$)$_2NC_6H_3$ | 4-$CH_3$ | H | i-$C_3H_7$ |
| 187 | 2,4-bis[($C_2H_5$)$_2$N]$C_6H_3$ | 3,4-(Cl)$_2$ | $CH_3O$ | N($C_2H_5$)$_2$ |
| 188 | 2-Cl—4-(i-$C_3H_7$)$_2NC_6H_3$ | 4-I | H | N($CH_3$)($C_6H_5CH_2$) |
| 189 | 2-I-4($C_4H_9$) ($C_6H_5CH_2$)$NC_6H_3$ | 4-$CH_3O$ | Br | H |
| 190 | 2-$CH_3$—4-($C_2H_5$)$_2NC_6H_3$ | 3-$NO_2$ | H | N(H) ($C_6H_5CH_2$) |
| 191 | 4-($C_2H_5$) ($C_6H_5CH_2$) $NC_6H_3$ | H | $CH_3$ | N($C_2H_5$)$_2$ |
| 192 | 2-$C_3H_7O$-4-($C_2H_5$)$_2NC_6H_3$ | 4-Br | F | H |
| 193 | 4-($CH_3$) ($C_3H_7$)$NC_6H_4$ | 4-Cl-3-$NO_2$ | $CH_3O$ | H |
| 194 | 2,4-bis[($C_4H_9$)$_2$N]$C_6H_3$ | 4-$CH_3$ | H | $C_2H_5O$ |
| 195 | 2-(i-$C_3H_7$)—4-($C_2H_5$)$_2NC_6H_3$ | H | $CH_3O$ | N($CH_3$)$_2$ |
| 196 | 4-($CH_3$)$_2NC_6H_4$ | 4-F | H | N($C_2H_5$)$_2$ |
| 197 | 2,4-bis[($CH_3$)$_2$N]$C_6H_3$ | 4-$CH_3$ | H | $CH_3$ |
| 198 | 9-julolidinyl | H | H | Cl |

It is contemplated that by following procedures similar to those described in the foregoing examples but employing the appropriate aldehyde of the formula Z-CHO, the appropriate 1-$R^8$-pyrrole and the appropriate R-phenylsulfinic acid, there will be obtained the [(Z)(1-$R^8$-2-pyrrolyl)(R-phenylsulfonyl)]methanes of Formulas XVII—XX, Examples 199–228, presented in Table J hereinbelow.

TABLE J

Methanes of Formulas XVII—XX

| Ex. | Z | R | $R^8$ |
|---|---|---|---|
| 199 | 2-Cl—$C_6H_4$ | 4-$CH_3$ | $C_6H_4$ |
| 200 | 4-$C_2H_5OC_6H_4$ | 4-H | $C_3H_7$ |
| 201 | 2,4-$(CH_3O)_2C_6H_3$ | 4-Cl | $C_2H_5$ |
| 202 | 4-i-$C_3H_7C_6H_4$ | 4-Cl-3-$NO_2$ | i-$C_3H_7$ |
| 203 | 4-$(CH_3)_2NC_6H_4$ | 4-Br | $CH_3$ |
| 204 | 2-$CH_3O$-4-$(C_2H_5)_2NC_6H_3$ | 4-$CH_3O$ | H |
| 205 | 4-$(CH_3)$ $(C_6H_5CH_2)NC_6H_4$ | 4-I | $C_3H_7$ |
| 206 | 2-Cl-4-$(CH_3)_2NC_6H_3$ | 4-$CH_3CONH$ | $C_6H_5$ |
| 207 | 1-$CH_3$-2-pyrrolyl | 4-$CH_3$ | $CH_3$ |
| 208 | 2-pyrrolyl | 4-$CH_3O$ | $C_2H_5$ |
| 209 | 1-ethyl-2-pyrrolyl | 4-$C_{12}H_{25}$ | i-$C_3H_7$ |
| 210 | 1-i-propyl-2-pyrrolyl | 4-Cl | $C_3H_7$ |
| 211 | 2-thienyl | 2,4-$(CH_3)_2$ | $C_6H_5$ |
| 212 | 2-thienyl | 3-$NO_2$ | H |
| 213 | 2-thienyl | 2,5-$(Cl)_2$ | $C_2H_5$ |
| 214 | 2-thienyl | H | $C_6H_4$ |
| 215 | 2-furanyl | 4-$CH_3CONH$ | $CH_3$ |
| 216 | 2-furanyl | 4-F | $C_2H_5$ |
| 217 | 2-furanyl | 2,5-$(CH_3)_2$ | $C_6H_5$ |
| 218 | 2-furanyl | 4-I | i-$C_3H_7$ |
| 219 | 3-carbazolyl | 4-$C_{12}H_{25}$ | $CH_3$ |
| 220 | 9-phenyl-3-carbazolyl | 4-Br | $C_2H_5$ |
| 221 | 9-ethyl-3-carbazolyl | 2-$NO_2$ | $C_6H_5$ |
| 222 | 9-propyl-3-carbazolyl | 3,4-$(Cl)_2$ | $C_3H_7$ |
| 223 | 2-pyridinyl | 4-$CH_3$ | H |
| 224 | 3-pyridinyl | 3-$NO_2$ | $CH_3$ |
| 225 | 4-pyridinyl | 4-Cl | $C_2H_5$ |
| 226 | 2-pyridinyl | 4-Cl-3-$NO_2$ | i-$C_3H_7$ |
| 227 | 3-pyridinyl | 4-$C_{12}H_{25}$ | $C_6H_5$ |
| 228 | 4-pyridinyl | H | $C_3H_7$ |

EXAMPLE 229

The use of the compounds of Formulas I, XI, XV and XVI described in Examples 1 through 228 as color forming components in pressure sensitive microencapsulated copying systems is illustrated with reference to the product of Example 1.

A. A mixture of 40 g of i-propylbiphenyl and 0.98 g of [(1-ethyl-2-methyl-3-indolyl)-(4-dimethylaminophenyl)-(4-methylphenylsulfonyl)]methane, prepared as described above in Example 1 was heated to 100° C. until a clear solution was formed and then cooled to approximately 50° C. A second solution of 3.35 g of carboxymethylcellulose dissolved in 134 ml of distilled water was prepared. A third solution containing 10 g of pigskin gelatin dissolved in 80 ml of distilled water was heated at approximately 50° C. for about one hour.

B. Two solutions, the first containing the product and the i-propylbiphenyl, and the second containing the carboxymethylcellulose and the water were mixed and emulsified using a variable speed one-half horsepower Eppenbach Homo-Mixer (Gifford-Wood Co., Hudson, N.Y.) for approximately five minutes until the particle size of the suspended emulsion was approximately 5 microns at approximately 50° C. While maintaining the rapid agitation, the third solution containing the gelatin and water was added and the pH adjusted to 6.5 with the addition of 10 percent aqueous sodium hydroxide. Slowly 447 ml of water at approximately 50° C. was added and the pH was adjusted to 4.5 by the addition of 10 percent aqueous acetic acid. After five minutes of rapid agitation the mixture was cooled to approximately 15° C. by means of an external ice/water bath and 6.6 ml of glutaraldehyde was added dropwise and agitation continued for 15 minutes. At this time, the Eppenbach Homo-Mixer was replaced with a conventional blade type laboratory agitator and the suspension was stirred overnight. The suspension was adjusted to 747 g with the addition of distilled water.

C. The stock microcapsule suspension prepared in part B above was coated on paper sheets to a thickness of approximately 0.0015 inch and the coated paper air dried. The paper thus coated with the microencapsulated colorless precursor was assembled as the top sheet in a manifold system by positioning the coated side in contact with the coated side of a commercially available receiving sheet coated with a color developer of the electron accepting type. More specifically, papers coated with a phenolic resin and with an acidic clay were employed in this test. An image was then drawn with a stylus on the top sheet bearing the microencapsulated colorless precursor on its reverse side causing the affected microcapsules to rupture thus allowing the solution of the colorless precursor held by said microcapsules to flow into contact with the color developing substance on the receiving sheet whereupon a bluish-red-colored image promptly formed. The developed image exhibited good tinctorial strength and excellent xerographic copiability characteristics.

When evaluated in a duplicating system prepared and tested as described above, the product of Example 18, [(2-furanyl)(1-ethyl-2-methyl-3-indolyl)(4-methylphenylsulfonyl)]methane, produced a yellow-colored image; the product of Example 19, [(2-thienyl)(1-ethyl-2-methyl-3-indolyl)(4-methylphenylsulfonyl)]methane, produced a yellow-colored image; the product of Example 8, [(1-methyl-2-pyrrolyl)(1-ethyl-2-methyl-3-indolyl)(4-methylphenylsulfonyl)]methane, produced a yellow-colored image; the product of Example 21, [bis(1-ethyl-2-methyl-3-indolyl)(4-methylphenylsulfonyl)]methane, produced an orange-colored image; and the product of Example 22, [(3-indolyl)(1-ethyl-2-methyl-3-indolyl)(4-methylphenylsulfonyl)]methane, produced an orange-colored image.

EXAMPLE 230

The utility of the compounds of Formulas I, XV and XVI whose preparations are described in the foregoing examples as color forming components in pressure-sensitive microencapsulated copying systems, is illustrated by the incorporation and testing of the compound of Example 1, [(1-ethyl-2-methyl-3-indolyl)(4-dimethylaminophenyl)(4-methylphenylsulfonyl)]methane in a pressure-sensitive marking paper. The test paper was prepared by a procedure described in U.S. Pat. 4,000,087.

A. A mixture of 5.9 g of a commercially-supplied polyvinyl alcohol having a hydrolysis of 87 to 89 percent and 250.0 ml of water were warmed until a clear solution was obtained. After cooling to room temperature, 40.0 ml of water was added.

B. A second solution was prepared by warming 5.9 g of a commercially-supplied epichlorohydrin/bisphenol A type solid epoxy resin in 41.8 g of dibutylphthalate until a clear solution resulted. After cooling slightly 3.0 g of [(1-ethyl-2-methyl-3-indolyl)(4-dimethylaminophenyl)(4-methylphenylsulfonyl)]methane, prepared as described in Example 1 above, was added and stirred until dissolved.

C. A mixture of 9.7 g of terephthaloyl chloride and 47.3 g of dibutylphthalate was heated until a clear solution resulted and then cooled to room temperature.

D. The dye-resin solution from part B above and the terephthaloyl chloride solution from part C above were mixed together and slowly added to the polyvinyl alcohol from part A above and emulsified with a variable speed one-half horsepower Eppenbach Homo-Mixer (Gifford-Wood Co., Hudson, N.Y.) for approximately one minute at an applied voltage of 30–40 until the particle size of the suspended emulsion was approximately 5 microns. The resulting emulsion was transferred to a suitable container with a variable speed conventional mechanical stirrer with a 50.0 ml of water wash. With stirring there was slowly added to the emulsion a solution consisting of 2.9 g of sodium carbonate and 5.5 g of diethylene triamine dissolved in 33.0 ml of water. The resulting suspension was stirred at room temperature for approximately eighteen hours. The pH was adjusted to 7-7.5 by the addition of 15 percent aqueous sodium carbonate and the stirring continued for approximately six hours. The total weight of the suspension was adjusted to 474 g with the addition of water if needed.

E. The stock microcapsule suspension prepared in part D above was coated on paper sheets using a #6 wire wound rod and the coated paper air dried. The paper thus coated with the microencapsulated colorless precursor was assembled as the top sheet in a manifold system by positioning the coated side in contact with the coated side of a commercially available receiving sheet coated with a color developer of the electron accepting type. More specifically, papers coated with a phenolic resin and with an acidic clay were employed in this test. An image was then drawn with a stylus on the top sheet bearing the microencapsulated colorless precursor on its reverse side causing the affected microcapsules to rupture thus allowing the solution of the colorless precursor held by said microcapsules to flow into contact with the color developing substance on the receiving sheet whereupon a bluish-red-colored image promptly formed. The developed image exhibited good tinctorial strength and excellent xerographic copiability characteristics.

When evaluated in a duplicating system prepared and tested as described above, the product of Example 18, [(2-furanyl)(1-ethyl-2-methyl-3-indolyl)(4-methylphenylsulfonyl)]methane, produced a yellow-colored image; the product of Example 19, [(2-thienyl)(1-ethyl-2-methyl-3-indolyl)(4-methylphenylsulfonyl)]methane, produced a yellow-colored image; the product of Example 8, [(1-methyl-2-pyrrolyl)(1-ethyl-2-methyl-3-indolyl)(4-methylphenylsulfonyl)]methane, produced a yellow-colored image; the product of Example 21, [bis(1-ethyl-2-methyl-3-indolyl)(4-methylphenylsulfonyl)]methane, produced an orange-colored image; the product of Example 22, [(3-indolyl)(1-ethyl-2-methyl-3-indolyl)(4-methylphenylsulfonyl)]methane, produced an orange-colored image; the product of Example 6, [bis(4-dimethylaminophenyl)(4-methylphenylsulfonyl)]methane, produced a blue-colored image; and the product of Example 39, [(4-dimethylaminophenyl)(2-ethoxy-4-diethylaminophenyl)(4methylphenylsulfonyl)]methane, produced a blue-colored image.

EXAMPLE 231

The utility of the compounds of Formulas I, XI, XV, and XVI whose preparations are described in the foregoing examples as color forming components in thermal marking systems is illustrated by the incorporation and testing of the compound of Example 1, [(1-ethyl-2-methyl-3-indolyl)-(4-dimethylaminophenyl)-(4-methylphenylsulfonyl)]methane in a thermal sensitive marking paper. The test paper was prepared by a procedure similar to that described in U.S. Pat. No. 3,539,375.

A. A mixture of 2.0 g of [(1-ethyl-2-methyl-3-indolyl)(4-dimethylaminophenyl)-(4-methylphenylsulfonyl)]methane, 8.6 g of a ten percent aqueous solution of polyvinyl alcohol (approximately 99 percent hydrolyzed), 3.7 g of water and 31.6 g of 1/16 inch diameter zirconium grinding beads was charged into a container which was placed in a mechanical shaker. Shaking was effected for one hour. The zirconium beads were then removed by straining the mixture through a No. 40 sieve.

B. Similarly, a mixture of 9.8 g of 4,4'-isopropylidine diphenol (Bisphenol A), 42.0 g of a ten percent aqueous polyvinyl alcohol solution (approximately 99 percent hydrolyzed), 18.2 g of water and 221.2 g of 1/16 inch diameter zirconium grinding beads was charged into a container which was placed in a mechanical shaker. After shaking was effected for one hour, the zirconium beads were removed by straining through a No. 40 sieve.

C. A coating composition was prepared by mixing 2.1 g of the slurry from A and 47.9 g of the slurry from B. The mixture was then uniformly coated on sheets of paper at a thickness of approximately 0.0015 inch and the coated sheets air-dried. The coated paper was tested by tracing a design on the coated side of the paper placed on a smooth flat surface with a stylus heated to approximately 120° C. A violet-colored image corresponding to the traced design promptly developed.

When evaluated in thermal marking paper prepared and tested as described above, the product of Example 19, [(2-thienyl)-(1-ethyl-2-methyl-3-indolyl)-(4-methylphenylsulfonyl)]methane, produced a light yellow-colored image at approximately 180° C.; the product of Example 2, [(1,2-dimethyl-3-indolyl)-(4-dimethylaminophenyl)-(4-methylphenylsulfonyl)]methane, produced a reddish-purple-colored image at approximately 105° C.; the product of Example 21, [bis(1-ethyl-2-methyl-3-indolyl)-(4-methylphenylsulfonyl)]methane, produced an orange-colored image at approximately 105° C. and a violet-red-colored image at 150° C.; the product of Example 8, [(1-methyl-2-pyrrolyl)-(4-dimethylaminophenyl)-(4-methylphenylsulfonyl)]methane, produced a reddish-orange-colored image at approximately 100° C.; the product of Example 10, [(2-phenyl-3-indolyl)-(4-dimethylaminophenyl)-(4-methylphenylsulfonyl)]methane, produced a blue-colored image at approximately 100° C.; the product of Example 38, [(4-dimethylaminophenyl)(4-N-ethyl-N-benzylaminophenyl)(4-methyphenylsulfonyl)]methane, produced a turquoise-colored image at approximately 160° C.; the product of Example 49, [(4-chlorophenyl)(1-methyl-2-pyrrole)(4-methylphenylsulfonyl)]methane, produced a rust-colored image; the product of Example 51, [(4-methoxyphenyl)(1-methyl-2-pyrrolyl))(benzenesulfonyl)]methane, produced an orange-colored image at 150° C.; the product of Example 55, [(2-thienyl)(1-methyl-2-pyrrolyl)(4-methylphenylsulfonyl)]methane, produced a pinkish-brown colored image at 150° C.; and the product of Example 57, [(9-ethyl-3-carbazolyl)(1-methyl-2-pyrrolyl)(4-methylphenylsulfonyl)]methane, produced a purple-red-colored image.

EXAMPLE 232

A. Proceeding in a manner similar to that described in Example 231 above, 2.0 g of the compound of Example 4, [(3-indolyl)(4-methylphenylsulfonyl)]methane was ground in a mixture of 8.6 of a ten percent aqueous solution of polyvinyl alcohol and 3.7 g of water.

B. A mixture of 9.8 g of 4,4′-isopropylidine diphenol (bisphenol A), 42.0 g of ten percent aqueous polyvinyl alcohol, 22.1 g of water and 221.6 g of 1/16 inch diameter zirconium grinding beads was ground for approximately one hour.

C. A coating composition was prepared by mixing 2.1 g of the slurry from A and 47.9 g of the slurry from B. The mixture was then uniformly coated on sheets of paper at a thickness of approximately 0.0015 inch and the coated sheets air-dried. The coated paper was tested by tracing a design on the coated side of the paper placed on a smooth flat surface with a stylus heated to approximately 130° C. A light blue-colored image corresponding to the traced design promptly developed.

When evaluated in thermal marking paper prepared and tested as described above, the product of Example 3, [(1-ethyl-2-methyl-3-indolyl)-(methyl)-(4-methylphenylsulfonyl)]methane, produced a light grape-colored image at approximately 130° C.

We claim:
1. A [(2-$R^5$-4-$R^6$-phenyl)(1-$R^1$-2-$R^2$-5/6-$R^3$-3-indolyl)(R-phenylsulfonyl)]methane of the formula

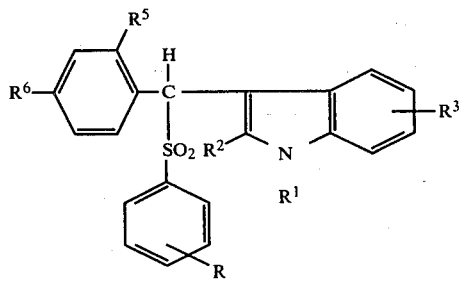

wherein:

R represents one or two of hydrogen, $C_1$ to $C_{12}$ alkyl, $C_1$ to $C_3$ alkoxy, halo, nitro or acetamido;

$R^1$ represents hydrogen, $C_1$ to $C_{18}$ alkyl, $C_2$ to $C_4$ alkenyl, benzyl or benzyl substituted in the benzene ring by one or two of halo or $C_1$ to $C_3$ alkyl;

$R^2$ represents hydrogen, $C_1$ to $C_3$ alkyl or phenyl;

$R^3$ represents one or two of hydrogen, $C_1$ to $C_3$ alkyl, $C_1$ to $C_3$ alkoxy, halo or nitro;

$R^5$ represents hydrogen, dialkylamino in which alkyl is non-tertiary $C_1$ to $C_4$ alkyl, $C_1$ to $C_3$ alkyl, $C_1$ to $C_4$ alkoxy or halo; and $R^6$ represents hydrogen, $C_1$ to $C_3$ alkyl, $C_1$ to $C_3$ alkoxy, halo, dialkylamino in which alkyl is non-tertiary $C_1$ to $C_4$ or N-alkylbenzylamino in which alkyl is non-tertiary $C_1$ to $C_4$ and benzyl may be substituted in the benzene ring by one or two of halo or $C_1$ to $C_3$ alkyl.

2. [(4-Dimethylaminophenyl)(1-ethyl-2-methyl-3-indolyl)(4-methylphenylsulfonyl)]methane according to claim 1.

3. [(4-Dimethylaminophenyl)(1,2-dimethyl-3-indolyl)(4-methylphenylsulfonyl)]methane according to claim 1.

4. [(4-Dimethylaminophenyl)(1-ethyl-2-methyl-3-indolyl)(phenylsulfonyl)]methane according to claim 1.

5. [(4-Methoxyphenyl)(1-ethyl-2-methyl-3-indolyl)(4-methylphenylsulfonyl)]methane according to claim 1.

6. [(4-Dimethylaminophenyl)(2-phenyl-3-indolyl)(4-methylphenylsulfonyl)]methane according to claim 1.

7. [(4-Dimethylaminophenyl)(3-indolyl)(4-methylphenylsulfonyl)]methane according to claim 1.

8. [(4-Dimethylaminophenyl)(2,5-dimethyl-3-indolyl)(4-methylphenylsulfonyl)]methane according to claim 1.

9. [(4-Chlorophenyl)(1-ethyl-2-methyl-3-indolyl)(4-methylphenylsulfonyl)]methane according to claim 1.

10. [(4-Methylphenyl)(1-ethyl-2-methyl-3-indolyl)(4-methylphenylsulfonyl)]methane according to claim 1.

11. [(4-N-Ethyl-N-benzylaminophenyl)(1-ethyl-2-methyl-3-indolyl)(4-methylphenylsulfonyl)]methane according to claim 1.

12. [(4-Dimethylaminophenyl)(1,2-dimethyl-3-indolyl)(4-methoxyphenylsulfonyl)]methane according to claim 1.

13. [(4-Dimethylaminophenyl)(1-ethyl-2-methyl-3-indolyl)(4-chlorophenylsulfonyl)]methane according to claim 1.

14. [(4-Dimethylaminophenyl)(1-ethyl-2-methyl-3-indolyl)(4-dodecylphenylsulfonyl)]methane according to claim 1.

15. [(4-Dimethylaminophenyl)(1-ethyl-2-methyl-3-indolyl)(4-acetamidophenylsulfonyl)]methane according to claim 1.

* * * * *